United States Patent [19]

Pazos et al.

[11] Patent Number: 4,847,141
[45] Date of Patent: Jul. 11, 1989

[54] SUPERABSORBENT THERMOPLASTIC COMPOSITIONS AND NONWOVEN WEBS PREPARED THEREFROM

[75] Inventors: Jose F. Pazos, Roswell; Sharon L. Greene, Alpharetta; Augusto Rodriguez, Roswell, all of Ga.

[73] Assignee: Kimberly-Clark Corporation, Neenah, Wis.

[21] Appl. No.: 161,073

[22] Filed: Feb. 26, 1988

Related U.S. Application Data

[62] Division of Ser. No. 945,405, Dec. 22, 1986, Pat. No. 4,767,825.

[51] Int. Cl.$^4$ .............................................. D03D 3/00
[52] U.S. Cl. .................... 428/226; 428/224; 428/225; 428/227; 428/229; 428/232; 428/233; 428/288; 428/296; 428/703
[58] Field of Search ............... 428/226, 224, 225, 232, 428/288, 296, 227, 229

[56] References Cited

U.S. PATENT DOCUMENTS

| | | | |
|---|---|---|---|
| 2,929,800 | 3/1960 | Hill, Jr. | 260/77.5 |
| 2,929,804 | 3/1960 | Steuber | 260/77.5 |
| 3,016,599 | 1/1962 | Perry, Jr. | 28/78 |
| 3,341,394 | 9/1967 | Kinney | 161/72 |
| 3,428,711 | 2/1969 | Hunt | 260/859 |
| 3,557,044 | 1/1971 | Bleasdale et al. | 260/32.6 |
| 3,692,618 | 9/1972 | Dorschner et al. | 161/72 |
| 3,704,198 | 11/1972 | Prentice | 161/148 |
| 3,755,527 | 8/1973 | Keller et al. | 264/210 F |
| 3,783,872 | 1/1974 | King | 128/290 R |
| 3,822,238 | 7/1974 | Blair et al. | 260/75 NK |
| 3,849,241 | 11/1974 | Butin et al. | 161/169 |
| 3,939,105 | 2/1976 | Jones, Jr. et al. | 260/2.5 AY |
| 3,939,123 | 2/1976 | Matthews et al. | 260/77.5 AM |
| 3,940,542 | 2/1976 | Knopf et al. | 428/364 |
| 4,100,324 | 7/1978 | Anderson et al. | 428/288 |
| 4,156,066 | 5/1979 | Gould | 528/73 |
| 4,156,067 | 5/1979 | Gould | 528/73 |
| 4,182,827 | 1/1980 | Jones et al. | 528/60 |
| 4,209,605 | 6/1980 | Hoy et al. | 528/54 |
| 4,255,550 | 3/1981 | Gould | 528/44 |
| 4,340,563 | 7/1982 | Appel et al. | 264/518 |
| 4,622,263 | 7/1986 | Ando et al. | |
| 4,724,184 | 2/1988 | Killian et al. | 428/227 |

FOREIGN PATENT DOCUMENTS

2154886 9/1985 United Kingdom .
2157703 10/1985 United Kingdom .

OTHER PUBLICATIONS

"Superfine Thermoplastic Fibers," Van A Wente, in Industrial and Engineering Chemistry, pp. 1342–1346.
"Manufacture of Superfine Organic Fibers", V. A. Wente et al., May 25, 1954, Naval Research Laboratory, Washington, D.C.
"Melt Blowing—A One-Step Process for New Nonwoven Products," Buntin et al., TAPPI, vol. 56, No. 4, Apr. 1973, pp. 74–77.

Primary Examiner—Theodore E. Pertilla
Attorney, Agent, or Firm—William E. Maycock

[57] ABSTRACT

A superabsorbent, thermoplastic polymeric composition comprising:
(A) from about 86 to about 98 percent by weight, based on the total weight of the composition, of a poly(oxyethylene) diol soft segment having a weight average molecular weight in the range of from about 5,000 to about 50,000; and
(B) from about 2 to about 14 percent by weight, based on the total weight of the composition, of a hard segment which has a melting point above ambient temperature and below the temperature at which decomposition of either the composition or the soft segment takes place, is essentially insoluble in water, and phase separates from the soft segment, said hard segment being selected from the group consisting of polyurethanes, polyamides, polyesters, polyureas, and combinations thereof;

wherein the soft and hard segments are covalently bound together by means of urethane, amide, ester, or secondary urea linkages or combinations thereof.

The compositions are especially well suited for the preparation of nonwoven webs by meltblowing, coforming and spunbonding processes.

49 Claims, 3 Drawing Sheets

SUPERABSORBENT THERMOPLASTIC COMPOSITIONS AND NONWOVEN WEBS PREPARED THEREFROM

This is a divisional application of application Ser. No. 945,405 filed on Dec. 22, 1986 now U.S. Pat. No. 4,767,825 issued 8-30-88.

CROSS-REFERENCES TO RELATED APPLICATIONS

Various of the compositions described in the present invention are employed as examples in copending and commonly assigned application Ser. No. 944,713, entitled MELTBLOWN, SUPERABSORBENT THERMOPLASTIC COMPOSITIONS, filed on 12/22/86, now U.S. Pat. No. 4,820,577 in the names of Michael T. Morman, Sharon L. Greene, Jose F. Pazos, and Augusto Rodriguez. Blends of the compositions of the present invention with other thermoplastic polymers, and nonwoven webs prepared therefrom, are described and claimed in copending and commonly assigned application Ser. No. 945,753, entitled THERMOPLASTIC POLYMER BLENDS AND NONWOVEN WEBS PREPARED THEREFROM, filed on 12/22/86, now U.S. Pat. No. 4,806,598 in the name of Michael T. Morman.

BACKGROUND OF THE INVENTION

The present invention relates to superabsorbent thermoplastic compositions and to meltblown or spunbonded webs prepared therefrom.

Disposable absorbent products such as diapers, sanitary napkins, tampons, incontinence products, and the like typically are comprised of a batt or absorbent portion which is wrapped with a liner. The batt typically is comprised primarily of cellulose fibers and the liner usually is a nonwoven web of a polyolefin such as polyethylene or polypropylene.

In the past, significant efforts have been made to find ways to make such disposable absorbent products more efficient or more appealing to the consumer. Much of such efforts have focused on increasing the absorbent capacity of the product on a unit mass basis while at the same time increasing the ability of the product to retain absorbed fluid. The ability of a product to remove and keep body fluids from the skin is perceived as a desirable attribute and is believed to be a factor in the reduction of such skin problems as diaper rash.

Such increased absorbent capacity and fluid retention typically have been accomplished by incorporating a superabsorbent material into the absorbent batt. The superabsorbent material usually is in particulate form. Unfortunately, particulate superabsorbents often migrate in or fall out of the absorbent product and/or exhibit gel-blocking, a phenomenon which prevents the migration of fluid into the central portion of the superabsorbent particle. Moreover, the use of particulate superabsorbents complicates the manufacturing process and the particulate nature of the superabsorbents limits the applications for the superabsorbents.

Superabsorbent materials, also referred to as hydrogels, frequently are based on acrylate and methacrylate polymers and copolymers. Other hydrogels are based on starch or a modified starch. Hydrogels prepared from hydrolyzed crosslinked polyacrylamides and crosslinked sulfonated polystyrenes or based on maleic anhydride (or similar compounds) have been described. Finally, still other hydrogels are based on polyoxyalkylene glycols and include polyurethane hydrogels.

The known polyoxyalkylene glycol-based superabsorbents generally tend to come within one of the following classes, at least in so for as they are reasonably related to the present invention:

(1) crosslinked poly(oxyalkylene) glycols;
(2) crosslinked isocyanate-capped poly(oxyalkylene) glycols, i.e., polyurethanes or polyureas;
(3) polyurethanes prepared from polyfunctional prepolymers or resins and diisocyanates;
(4) polyurethanes prepared from isocyanate-capped polyesters or poly(oxyalkylene) glycols and difunctional extenders;
(5) polyurethanes prepared from poly(oxyalkylene) glycols, isocyanate-capped low molecular weight prepolymers, and polyfunctional low molecular weight components.

Class 1—Crosslinked Poly(oxyalkylene) Glycols

U.S. Pat. No. 3,783,872 describes absorbent pads containing insoluble hydrogels. The hydrogels can be present in the pads as a powder or as a film. The hydrogels are comprised of crosslinked poly(alkylene oxide). Suitable materials are stated to include, by way of illustration, a poly(alkylene oxide), such as poly(ethylene oxide); poly(vinyl alcohol); poly(vinyl methyl ether); copolymers of maleic anhydride and ethylene; and copolymers of maleic anhydride and vinyl methyl ether. The polymers are crosslinked by ionizing radiation.

An apparently preferred group of polymers includes poly(ethylene oxide), copolymers of ethylene oxide and propylene oxide, and alkyl-substituted phenyl ethers of ethylene oxide polymers in which the alkyl groups may be methyl and/or butyl.

The polymers which can be used also are described in terms of reduced viscosity, rather than by molecular weight. The polymers apparently can have average molecular weights of less than about 150,000 to more than about 10,000,000.

Class 2—Crosslinked Isocyanate-Capped Poly(oxyalkylene) Glycols, i.e., Polyurethanes or Polyureas U.S. Pat. No. 3,939,105 describes microporous polyurethane hydrogels. The hydrogels are the reaction products of a poly(oxyalkylene) polyol having an average molecular weight of up to about 25,000 and organic diisocyanate which have been lightly crosslinked with water or an organic amine. In practice, the polyol is reacted with the diisocyanate to give an isocyanate-capped polyol. Before the isocyanate-capped polyol is crosslinked, a liquid nonsolvent is added thereto in an amount which will not result in precipitation. It is the addition of the nonsolvent which results in the production of the microporous hydrogel. The nonsolvent typically is an aliphatic hydrocarbon or a dialkyl ether.

The disclosure of U.S. Pat. No. 3,939,123 is similar to that of the foregoing patent, except that a nonsolvent is not employed.

In a variation of the procedures disclosed in the two preceding patents, U.S. Pat. No. 3,940,542 describes the extrusion of a solution of the isocyanate-capped poly(oxyalkylene) polyol of such preceding patents into a coagulant or crosslinking bath containing water or an organic polyamine as a crosslinking agent to produce water swellable, lightly crosslinked hydrogel polymer tapes or fibers. U.S. Pat. No. 4,209,605 describes another variation in which hydrogels are produced by charging preselected feeds containing the poly(alkyleneoxy) polyol, diisocyanate, and catalyst to a reaction zone, extruding the resulting high viscosity polymer through a suitable die, and allowing crosslinking to take place by exposure to atmospheric humidity.

U.S. Pat. No. 4,182,827 describes a method of increasing the wetting rates of the hydrogels disclosed in the above three patents. The wetting rates are enhanced by treating the surface of the solid hydrogel with certain ketones, alcohols, organic amines, aromatic hydrocarbons, or aqueous alkali metal hydroxide solutions.

Class 3—Polyurethanes Prepared from Polyfunctional Prepolymers or Resins and Diisocyanates Hydrophilic polyurethane polymers are described in U.S. Pat. No. 3,822,238. They are prepared by reacting a diisocyanate with a polyfunctional prepolymer or resin. The prepolymer or resin can be, among other things, an adduct of ethylene oxide, propylene oxide, ethylene imine, propylene amine, dioxolane, or a mixture thereof with a polyhydroxy compound; a hydroxy carboxylic acid; a low molecular weight, hydrolyzed poly(vinyl acetate), polyacrylic acid, or polymethacrylic acid; or mixtures thereof. Examples of polyhydroxy compounds include ethylene glycol, propylene glycol, glycerol, trimethylolpropane, erythritol, pentaerythritol, anhydroenneaheptitol, sorbitol, mannitol, sucrose, and lactose. See also U.S. Pat. No. 3,975,350 which describes a carrier system employing the hydrophilic polyurethane polymers of the first patent.

Class 4—Polyurethanes Prepared from Isocyanate-Capped Polyesters or Poly(oxyalkylene) Glycols and Difunctional Extenders Segmented urethane polymers are described in U.K. patent application GB No. 2,154,886A. Briefly, a polyester or polyether glycol having a molecular weight of at least about 200 is reacted with an excess of organic diisocyanate to form an isocyanate-terminated prepolymer. The prepolymer then is reacted with a difunctional extender and, optionally, with a very small proportion of a monofunctional material which acts as a molecular weight regulator.

A polyether glycol apparently is preferred, such as a poly(tetramethylene ether) glycol having a molecular weight above about 600, e.g., from about 800 to about 5000.

The diisocyanate usually is an aromatic diisocyanate such as 4,4'-diphenylmethane diisocyanate and toluene diisocyanate. An excess of diisocyanate is employed, e.g., from about 1.2 to about 1.9 moles of diisocyanate per mole of glycol.

The difunctional extender has two groups which are reactive with isocyanates. The extender can be a diol, an amine having at least one amino hydrogen per amino group, or water. Examples of suitable extenders include water, 1,4-butanediol, diethylene glycol, ethylene glycol, ethylenediamine, diphenylmethane diamine, 1,3-cyclohexylene diamine, 1,4-cyclohexylene diamine, and the like.

Similar polymers are described in U.S. Pat. Nos. 2,929,800, 2,929,804, 3,428,711, and 3,557,044.

Class 5—Polyurethanes Prepared from Poly(oxyalkylene) Glycols, Isocyanate-Capped Low Molecular Weight Prepolymers, and Polyfunctional Low Molecular Weight Components A polyurethane similar to the polyurethane hydrogels described above is disclosed in U.K. patent application GB No. 2,157,703A. The material is described as useful for coating fabrics and clothing, with no mention of water-absorbing properties. According to the reference, the polyurethane is formed from a reaction mixture comprising an isocyanate-terminated prepolymer, a polyol component containing at least 25 percent by weight of polyoxyethylene units based on the total weight of constituents, and a low molecular weight constituent having an active hydrogen functionality of at least two. If desired, the viscosity of the reaction mixture can be increased by adding one or more additional low molecular weight constituents having a functionality of at least two and preferably three; in the preferred case, it is clear that the additional constituent is functioning as a crosslinking agent.

The prepolymer is formed from the reaction product of a polyisocyanate containing at least two isocyanate groups per molecule with a low molecular weight component having an active hydrogen functionality of at least two. Such component can be a diamine, dihydrazide, diamide, diol, dithiol, dicarboxylic acid, disulfonic acid, or a mixture thereof. Diols are preferred, with representatives examples including thiodiglycol, ethylene glycol, diethylene glycol, and 1,4-butanediol. Trifunctional compounds can be included, such as trimethylolpropane, diethylenetriamine, and compounds having two or more different types of functional groups. Preferably, such low molecular weight component has a molecular weight of not more than 200.

The polyisocyanate used to prepare the prepolymer can be any of those known to be useful for preparing polyurethanes. Examples include toluene-2,4-diisocyanate, toluene-2,6-diisocyanate, mixtures of the foregoing two compounds, 1,6-hexamethylenediisocyanate, 1,5-naphthalenediisocyanate, 4,4'-diphenylmethanediisocyanate, 1,4-cyclohexanediisocyanate, 1,4-phenylenediisocyanate, m- and p-tetramethylxylyldiisocyanates and mixtures thereof, isophoronediisocyanate, and 4,4'dicyclohexylmethanediisocyanate. The last two compounds are preferred.

The polyol component contains at least 25 percent polyoxyethylene units. The preferred polyoxyethylene-containing compound is a polyethylene glycol having a molecular weight of from about 400 to about 2000. Other suitable compounds include block copolymers of ethylene oxide with other 1,2-alkylene oxides, such as propylene oxide and butylene oxide; and copolymers formed by reaction of ethylene oxide with polyols, polyamines, and polythiols.

The polyol component may consist in part of substances which do not contain polyoxyethylene units, such as polyester polyols and polyether polyols. Examples of the former include polycaprolactone diols and polyesters prepared from a dicarboxylic acid such as oxalic, maleic, succinic, adipic, suberic, sebacic, and the isomeric phthalic acids and a polyol such as ethylene glycol, diethylene glycol, 1,4-butanediol, 1,6-hexanediol, mixtures thereof, glycerol, trimethylolpropane, pentaerythritol, sorbitol, and sucrose. An example of the latter, which is preferred, is polytetramethylene glycol.

The low molecular weight constituent in general can be the same type of compound as the low molecular weight component already described.

If desired, crosslinking agents such as triisocyanates and melamine-formaldehyde resins also can be employed.

SUMMARY OF THE INVENTION

It now has been unexpectedly discovered that certain compositions similar to those of Class 4, but based on a difunctional poly(oxyethylene) having a molecular weight greater than about 5,000, can be formed into nonwoven webs or fabrics, particularly by meltblowing or spunbonding and that these compositions (unlike those of Class 4) are superabsorbent.

Accordingly, it is an object of the present invention to provide a superabsorbent, thermoplastic polymeric composition.

It is another object of the present invention to provide a superabsorbent, thermoplastic polyurethane composition.

It is a further object of the present invention to provide a superabsorbent nonwoven web.

Yet another object of the present invention is to provide a superabsorbent polyurethane nonwoven web. A further object of the present invention is to provide a meltblown or spunbonded superabsorbent polyurethane nonwoven web.

Still another object of the invention is to provide a coformed meltblown superabsorbent polyurethane nonwoven web.

These and other objects will be readily apparent to those having ordinary skill in the art from a reading of the specification and claims which follow.

Accordingly, the present invention provides a superabsorbent, thermoplastic polymeric composition comprising:

(a) from about 86 to about 98 percent by weight, based on the total weight of the composition, of a poly(oxyethylene) soft segment having a weight average molecular weight in the range of from about 5,000 to about 50,000; and (b) from about 2 to about 14 percent by weight, based on the total weight of the composition, of a hard segment which has a melting point above ambient temperature and below the temperature at which decomposition of either the composition or the soft segment takes place, is essentially insoluble in water, and phase separates from the soft segment, said hard segment being selected from the group consisting of polyurethanes, polyamides, polyesters, polyureas, and combinations thereof;

wherein the soft and hard segments are covalently bound together by means of urethane, amide, ester, or secondary urea linkages or combinations thereof.

The present invention also provides a superabsorbent, thermoplastic polymeric composition having the following general formula:

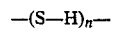

in which S represents

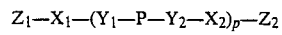

and H represents

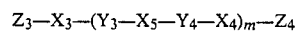

wherein P represents a poly(oxyethylene) moiety having a weight average molecular weight of from about 5,000 to about 50,000; each of $Y_1$, $Y_2$, $Y_3$, and $Y_4$ independently represents a urethane, amide, ester, or secondary urea linkage; each of $X_1$, $X_2$, $X_3$, $X_4$, and $X_5$ independently represents a divalent aliphatic, cycloaliphatic, aromatic, or heterocyclic group; each of $Z_1$, $Z_2$, $Z_3$, and $Z_4$ independently represents a monovalent functional group which is reactive with another functional group to give a urethane, amide, ester, or secondary urea linkage; m is an integer of from 0 to about 50; n is an integer of from about 1 to about 20; p is an integer of from about 1 to about 10; S represents from about 86 to about 98 percent by weight of the total composition; and H represents from about 2 to about 14 percent by weight of the total composition and has a melting point above ambient temperature and below the temperature at which decomposition of either the composition or the soft segment takes place, is essentially insoluble in water, and phase separates from the soft segment, said hard segment being selected from the group consisting of polyurethanes, polyamides, polyesters, polyureas, and combinations thereof.

The present invention also provides a nonwoven web comprising fibers composed of a superabsorbent, thermoplastic polymeric composition comprising:

(A) from about 86 to about 98 percent by weight, based on the total weight of the composition, of a poly(oxyethylene) soft segment having a weight average molecular weight in the range of from about 5,000 to about 50,000; and (B) from about 2 to about 14 percent by weight, based on the total weight of the composition, of a hard segment which has a melting point above ambient temperature and below the temperature at which decomposition of either the composition or the soft segment takes place, is essentially insoluble in water, and phase separates from the soft segment, said hard segment being selected from the group consisting of polyurethanes, polyamides, polyesters, polyureas, and combinations thereof;

wherein the soft and hard segments are covalently bound together by means of urethane, amide, ester, or secondary urea linkages or combinations thereof.

The present invention further provides a nonwoven web comprising a plurality of substantially identically prepared discontinuous and substantially randomly deposited monofilaments of a superabsorbent, thermoplastic polymeric composition comprising:

(A) from about 86 to about 98 percent by weight, based on the total weight of the composition, of a poly(oxyethylene) soft segment having a weight average molecular weight in the range of from about 5,000 to about 50,000; and (B) from about 2 to about 14 percent by weight, based on the total weight of the composition, of a hard segment which has a melting point above ambient temperature and below the temperature at which decomposition of either the composition or the soft segment takes place, is essentially insoluble in water, and phase separates from the soft segment, said hard segment being selected from the group consisting of polyurethanes, polyamides, polyesters, and polyureas, and combinations thereof; wherein the soft and hard segments are covalently bound together by means of urethane, amide, ester, or secondary urea linkages or combinations thereof.

The present invention additionally provides a nonwoven web comprising a plurality of substantially identically prepared continuous and substantially randomly deposited monofilaments of a superabsorbent, thermoplastic polymeric composition comprising:
- (A) from about 86 to about 98 percent by weight, based on the total weight of the composition, of a poly(oxyethylene) soft segment having a weight average molecular weight in the range of from about 5,000 to about 50,000; and
- (B) from about 2 to about 14 percent by weight, based on the total weight of the composition, of a hard segment which has a melting point above ambient temperature and below the temperature at which decomposition of either the composition or the soft segment takes place, is essentially insoluble in water, and phase separates from the soft segment, said hard segment being selected from the group consisting of polyurethanes, polyamides, polyesters, polyureas, and combinations thereof;

wherein the soft and hard segments are covalently bound together by means of urethane, amide, ester, or secondary urea linkages or combinations thereof.

In preferred embodiments, the hard segment is a polyurethane. In other preferred embodiments, the hard segment is a polyurethane based on 1,4-butanediol.

The present invention also provides a nonwoven web comprising a matrix of meltblown thermoplastic polymeric fibers and a multiplicity of individualized fibers disposed throughout said matrix and engaging at least some of the matrix fibers to space said matrix fibers apart from each other, said individualized fibers being interconnected by and held captive within said matrix by mechanical entanglement of said matrix fibers with said individualized fibers, the mechanical entanglement and interconnection of said matrix fibers and individualized fibers alone forming a coherent integrated fibrous structure, in which either said matrix fibers or said individualized fibers are composed of a superabsorbent, thermoplastic polymeric composition comprising:
- (A) from about 86 to about 98 percent by weight, based on the total weight of the composition, of a poly(oxyethylene) soft segment having a weight average molecular weight in the range of from about 5,000 to about 50,000; and
- (B) from about 2 to about 14 percent by weight, based on the total weight of the composition, of a hard segment which has a melting point above ambient temperature and below the temperature at which decomposition of either the composition or the soft segment takes place, is essentially insoluble in water, and phase separates from the soft segment, said hard segment being selected from the group consisting of polyurethanes, polyamides, polyesters, polyureas, and combinations thereof;

wherein the soft and hard segments are covalently bound together by means of urethane, amide, ester, or secondary urea linkages or combinations thereof.

In preferred embodiments, the hard segment is a polyurethane. In other preferred embodiments, the hard segment is a polyurethane based on 1,4-butanediol.

Finally, the present invention provides a method of preparing a superabsorbent, thermoplastic polymeric composition which comprises:
- (A) reacting a first compound with a second compound at a temperature of from about 50 to about 200 degrees C. for a time sufficient to effect essentially complete reation; and
- (B) reacting with the product from step A a third compound at a temperature of from about 80 to about 200 degrees C. for a time sufficient to obtain a melt flow rate of less than about 1,000 g per 10 minutes under the test conditions described hereinafter;

in which said first compound is a difunctional poly(oxyethylene) having a weight average molecular weight of from about 5,000 to about 50,000; said second compound is an aliphatic, cycloaliphatic, aromatic, or heterocyclic compound having two functional groups which are reactive with the functional groups of said first compound; the mole ratio of said second compound to said first compound is in the range of from about 2 to about 100; said third compound is an aliphatic, cycloaliphatic, aromatic, heterocyclic, or polymeric compound having two functional groups which are reactive with the functional groups of said second compound; the reaction product of said first compound with said second compound, excluding excess second compound, is from about 86 to about 98 percent by weight of the final composition; and said third compound plus the excess of said second compound are from about 2 to about 14 percent by weight of the final composition.

In preferred embodiments, said second compound is an aliphatic or aromatic diisocyanate. In other preferred embodiments, said third compound is an aliphatic or aromatic diol having from 2 to about 24 carbon atoms.

DETAILED DESCRIPTION OF THE INVENTION

Figure 1:
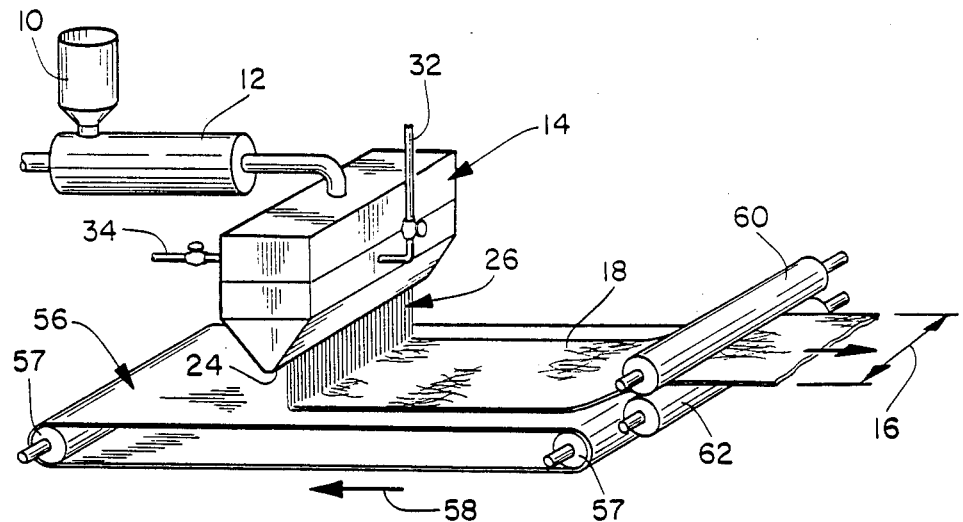
FIG. 1 is a perspective schematic view illustrating one embodiment of a process for forming a nonwoven web in accordance with the present invention.

Although the term "superabsorbent" has been used rather loosely in the prior art, the term is used herein to mean that the composition absorbs at least about 10 g of water per g of composition (10 g/g).

The superabsorbent, thermoplastic polymeric composition of the present invention comprises a soft segment and a hard segment, each segment being described herein in terms of segment constituents or composition and by general formula.

The soft segment typically comprises from about 86 to about 98 percent by weight of the total composition. Preferably, the soft segment comprises from about 90 to about 97 percent by weight, and most preferably from about 95 to about 97 percent by weight, of the total composition.

In general, the soft segment is based on a first compound having a weight average molecular weight of from about 5,000 to about 50,000. Preferably, the molecular weight of the first compound will be in the range of from about 8,000 to about 50,000, more preferably from about 8,000 to about 30,000, and most preferably from about 8,000 to about 16,000.

More particularly, the first compound is a difunctional poly(oxyethylene). The functional groups can be any group which will react with a second compound to give urethane, amide, ester, or secondary urea linkages, with urethane linkages being preferred. Examples of suitable functional groups include hydroxy, carboxy, amino, epoxy, imino, isocyanate, and the like. Preferably, both groups will be the same, and most preferably, both groups will be hydroxy groups.

When both functional groups of the first compound are hydroxy groups, the first compound will be a poly(oxyethylene) diol which is most preferred. Other functional groups can be present, however, either through direct synthesis or by reacting a poly(oxyethylene) diol with a modifier, with the latter procedure being preferred. However, a modifier does not have to introduce functional groups other than hydroxy groups. By way of illustration, a diol will be obtained upon reacting a poly(oxyethylene) diol with propylene oxide or a hydroxy-substituted carboxylic acid.

The use of a modifier involves procedures already known to those having ordinary skill in the art. To illustrate further, reacting a poly(oxyethylene) diol with ethylenimine will give a poly(oxyethylene) diamine. A diamine also will be obtained upon reacting the diol with an amino-substituted carboxylic acid. For convenience, a first compound obtained from the use of a modifier will be referred to herein as a modified poly(oxyethylene) diol, even though the functional groups present may not be hydroxy groups. Such term also is meant to include a poly(oxyethylene) having two functional groups other than hydroxy which was prepared by means other than through the use of a modifier. Similarly, the term "poly(oxyethylene) diol" is not to be limited to a diol which is the polycondensation product of ethylene oxide; rather, the term includes any diol composed substantially of a plurality of oxyethylene units, including a diol prepared by covalently coupling together two or more molecules of a poly(oxyethylene) diol by means of a coupling reagent, such as a diisocyanate.

The soft segment comprises the reaction product of first compound with second compound; excess second compound which may be present is not a part of the soft segment. Thus, the soft segment is a second compound-terminated poly(oxyethylene). The linkages by which the first compound is covalently bound to the second compound will be selected independently from the group consisting of urethane, amide, ester, and secondary urea linkages. Preferably, such linkages will be the same, and most preferably such linkages will be urethane linkages.

The second compound can be any compound having two functional groups which are reactive with the functional groups of the first compound to give urethane, amide, ester, and secondary urea linkages, provided only that the properties of the resulting soft segment are not significantly adversely affected by the choice of second compound. Thus, the second compound can be aliphatic, cycloaliphatic, aromatic, or heterocyclic. Moreover, for any given first compound functional group, one having ordinary skill in the art will be able to select appropriate functional groups for the second compound.

As already noted, the reaction between the first compound and the second compound preferably will result in the formation of urethane linkages. Since the preferred functional groups of the first compound are hydroxy groups, it follows that the preferred functional groups of the second compound are isocyanate groups. Thus, the most preferred second compounds are diisocyanates.

By way of illustration only, suitable diisocyanates which can be employed as the preferred second compound include toluene-2,4-diisocyanate, toluene-2,6-diisocyanate, ethylidene diisocyanate, propylene-1,2,-diisocyanate, cyclohexylene-1,2-diisocyanate, cyclohexylene-1,4-diisocyanate, m-phenylene diisocyanate, 4,4'-biphenylene diisocyanate, 3,3'-dichloro-4,4'-biphenylene diisocyanate, 1,4-tetramethylene diisocyanate, 1,6-hexamethylene diisocyanate, 1,10-decamethylene diisocyanate, xylene diisocyanate, chlorophenylene diisocyanate, diphenylmethane-4,4'-diisocyanate, naphthalene-1,5-diisocyanate, cumene-2,4-diisocyanate, 4-methoxy-1,3-phenylene diisocyanate, 4-chloro-1,3-phenylene diisocyanate, 4-bromo-1,3-phenylene diisocyanate, 4-ethoxy-1,3-phenylene diisocyanate, 2,4-diisocyanatodiphenyl ether, 5,6-dimethyl-1,3-phenylene diisocyanate, 2,4-dimethyl-1,3-phenylene diisocyanate, 4,4'-diisocyanatodiphenyl ether, benzidine diisocyanate, xylene-alpha, alpha'-diisothiocyanate, 3,3'-dimethyl-4,4'-biphenylene diisocyanate, 2,2',5,5'-tetramethyl-4,4'-biphenylene diisocyanate, 4,4'-methylenebis(phenylisocyanate), 4,4'-sulfonylbis(phenylisocyanate), 4,4'-methylene di-o-tolylisocyanate, 1,4-bis(2-isocyanatoisopropyl)benzene, ethylene diisocyanate, trimethylene diisocyanate, mixtures thereof, and the like.

The most preferred second compounds are toluene-2,-4diisocyanate, toluene-2,6-diisocyanate, mixtures of toluene-2,4- and toluene-2,6-diisocyanates, 4,4'-methylenebis(phenylisocyanate), and 1,6-hexamethylene diisocyanate.

The hard segment generally comprises from about 2 to about 14 percent by weight of the total composition. Preferably, the hard segment comprises from about 3 to about 10 percent by weight and most preferably from about 3 to about 5 percent by weight, of the total composition.

The hard segment must have a melting point above ambient temperature and below the temperature at which decomposition of either the composition or the soft segment takes place. In addition, the hard segment must be essentially insoluble in water and must phase separate from the soft segment.

The hard segment is selected from the group consisting of polyurethanes, polyamides, polyesters, polyureas, and combinations thereof. The hard segment can be polymeric ab initio or prepared in situ by the reaction between second compound and a third compound. Regardless of how the hard segment is prepared, polyurethanes are preferred. Most preferably, the hard segment is obtained by reacting second compound with a third compound.

Stated differently, the third compound can be either polymeric or monomeric. In either case, it is the reaction between the functional groups of the third compound with those of the second compound which results in the covalent linkage joining the hard and soft segments together. When the third compound is monomeric, excess second compound should be present in order for a condensation polymerization reaction to occur between the third compound and the excess second compound; such polycondensation reaction often is desired in order to obtain the appropriate properties for the hard segment.

As already noted, monomeric third compounds are preferred. If desired, a mixture of two or more third compounds can be employed. In addition, mixtures of one or more monomeric third compounds with one or more polymeric third compounds also are contemplated and come within the scope of the present invention.

In general, the third compound can be any compound having two functional groups which are reactive with second compound to from urethane, amide, ester, or secondary urea linkages. Thus, the third compound can be aliphatic, cycloaliphatic, aromatic, or heterocyclic.

The functional groups of the third compound can be any of those listed for the first compound. Preferably, the functional groups of the third compound will be of the same type as those of the first compound. Thus, the preferred functional groups of the third compound are hydroxy groups.

The most preferred third compounds are aliphatic and aromatic diols having from 2 to about 24 carbon atoms. Examples of suitable most preferred third compounds include, among others, ethylene glycol, 1,3-propanediol, 1,2-butanediol, 1,3-butanediol, 1,4-butanediol, 1,3-pentanediol, 1,5-pentanediol, 1,6-hexanediol, 1,6-heptanediol, 1,4-dodecanediol, 1,16-hexadecanediol, resorcinol, 4-hydroxymethylphenol, 1,4-bis(2-hydroxyethyl)benzene, 1,3-bis(2-hydroxyethyl)benzene, bis(2-hydroxyethyl) terephthalate, and the like.

The superabsorbent, thermoplastic polymeric composition of the present invention can be represented by the following general formula:

$$—(S—H)_n— \qquad (1)$$

in which S represents

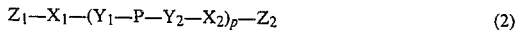
$$Z_1—X_1—(Y_1—P—Y_2—X_2)_p—Z_2 \qquad (2)$$

and H represents

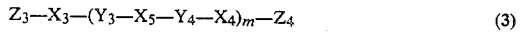
$$Z_3—X_3—(Y_3—X_5—Y_4—X_4)_m—Z_4 \qquad (3)$$

wherein P represents a poly(oxyethylene) moiety; each of $Y_1$, $Y_2$, $Y_3$, and $Y_4$ independently represents a urethane, amide, ester, or secondary urea linkage; each of $X_1$, $X_2$, $X_3$, $X_4$, and $X_5$ independently represents a divalent aliphatic, cycloaliphatic, aromatic, or heterocyclic group; each of $Z_1$, $Z_2$, $Z_3$, and $Z_4$ independently represents a monovalent functional group which is reactive with another functional group to give a urethane, amide, ester, or secondary urea linkage; m is an integer of from 0 to about 50; n is an integer of from about 1 to about 20; p is an integer of from about 1 to about 10; S represents from about 86 to about 98 percent by weight of the total composition and has a weight average molecular weight of from about 5,000 to about 50,000; and H represents from about 2 to about 14 percent by weight of the total composition and has a melting point above ambient temperature and below the temperature at which decomposition of either the composition or the soft segment takes place, is essentially insoluble in water, and phase separates from the soft segment, said hard segment being selected from the group consisting of polyurethanes, polyamides, polyesters, polyureas, and combinations thereof.

Formulas 1–3, above, necessarily represent the ideal. For example, formula 1 does not include the terminal moieties. In addition, because not all of the polymer molecules have the same length (or molecular weight), the values for m, n, and p rarely are whole numbers; such values typically are expressed as decimal fractions which represent average values. Consequently, the term "integer" as used herein is meant to include both whole numbers and decimal fractions.

According to formulas 2 and 3, each of the first, second, and third compounds can have two different functional groups. As a practical matter, however, this rarely will be the case. Consequently, typically $X_1 = X_2$, $Y_1 = Y_2$, $Z_1 = Z_2$, $X_3 = X_4$, $Y_3 = Y_4$, and $Z_3 = Z_4$. Moreover, usually $X_5 = X_1$ and $Y_3 = Y_1$. Under these circumstances, formulas 2 and 3 can be rewritten as formulas 4 and 5, respectively:

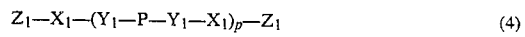
$$Z_1—X_1—(Y_1—P—Y_1—X_1)_p—Z_1 \qquad (4)$$

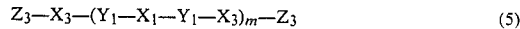
$$Z_3—X_3—(Y_1—X_1—Y_1—X_3)_m—Z_3 \qquad (5)$$

It should be apparent to one having ordinary skill in the art that the terminal moieties of the polymeric composition can be either soft segment or hard segment. When the terminal moieties are soft segment, formulas 4 and 5 can be combined to give formula 6:

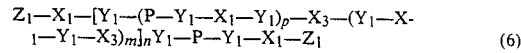
$$Z_1—X_1—[Y_1—(P—Y_1—X_1—Y_1)_p—X_3—(Y_1—X_1—Y_1—X_3)_m]_n Y_1—P—Y_1—X_1—Z_1 \qquad (6)$$

Similarly, formula 7 results when the terminal moieties are hard segment:

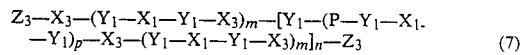
$$Z_3—X_3—(Y_1—X_1—Y_1—X_3)_m—[Y_1—(P—Y_1—X_1—Y_1)_p—X_3—(Y_1—X_1—Y_1—X_3)_m]_n—Z_3 \qquad (7)$$

There necessarily is a relationship between the molecular weight of the soft segment (or first compound) and the amount of hard segment which is present in the composition. The amount of hard segment present in turn is partly a function of the value of m, i.e., the number of repeating units in the hard segment. The amount of hard segment present in the composition also is a function of the mole ratio of soft segment to hard segment. Thus, the mole ratio of soft segment to hard segment can vary from 2 to 0.5. Mole ratios of 2 and 0.5 will result in compositions represented by formulas 6 and 7, respectively. Mole ratios greater than 2 or less than 0.5 will result in the presence in the composition of unreacted soft segment or unreacted hard segment, respectively.

These relationships are illustrated for compositions based on a poly(oxyethylene) diol, 4,4'-methylenebis(phenylisocyanate), and 1,4-butanediol, i.e., compositions representative of those prepared in the examples. The relationships are summarized in Tables 1–6, inclusive, which show the percent hard segment present in the composition for a soft segment of a given molecular weight and different values of m at each of three soft segment:hard segment (S:H) mole ratios. The soft segment and hard segment molecular weights were calculated from formulas 2 and 3, respectively.

TABLE 1

Percent Hard Segment in Compositions
Based on 8,500 M.W. Soft Segment

| | Percent Hard Segment S:H Mole Ratio | | |
|---|---|---|---|
| Value of m | 2 | 1 | 0.5 |
| 0 | 0.5 | 1.0 | 2.1 |
| 1 | 2.5 | 4.8 | 9.2 |
| 2 | 4.3 | 8.3 | 15.3 |
| 3 | 6.1 | 11.6 | 20.7 |
| 4 | 7.9 | 14.6 | 25.4 |
| 5 | 9.5 | 17.4 | 29.6 |
| 6 | 11.1 | 20.0 | 33.4 |
| 7 | 12.7 | 22.5 | 36.8 |
| 8 | 14.2 | 24.8 | 39.8 |

TABLE 2

Percent Hard Segment in Compositions
Based on 14,500 M.W. Soft Segment

| | Percent Hard Segment S:H Mole Ratio | | |
|---|---|---|---|
| Value of m | 2 | 1 | 0.5 |
| 0 | 0.3 | 0.6 | 1.2 |
| 1 | 1.5 | 2.9 | 5.6 |
| 2 | 2.6 | 5.0 | 9.6 |
| 3 | 3.7 | 7.1 | 13.3 |
| 4 | 4.8 | 9.1 | 16.7 |
| 5 | 5.8 | 11.0 | 19.8 |
| 6 | 6.8 | 12.8 | 22.7 |
| 7 | 7.8 | 14.6 | 25.4 |
| 10 | 10.7 | 19.4 | 32.5 |
| 14 | 14.3 | 25.1 | 40.1 |

TABLE 3

Percent Hard Segment in Compositions
Based on 16,750 M.W. Soft Segment

| | Percent Hard Segment S:H Mole Ratio | | |
|---|---|---|---|
| Value of m | 2 | 1 | 0.5 |
| 0 | 0.3 | 0.5 | 1.1 |
| 1 | 1.3 | 2.5 | 4.9 |
| 2 | 2.2 | 4.4 | 8.4 |
| 3 | 3.2 | 6.2 | 11.7 |
| 4 | 4.1 | 8.0 | 14.8 |
| 5 | 5.1 | 9.7 | 17.6 |
| 6 | 6.0 | 11.3 | 20.3 |
| 7 | 6.9 | 12.9 | 22.8 |
| 8 | 7.7 | 14.4 | 25.1 |
| 12 | 11.1 | 19.9 | 33.2 |
| 16 | 14.2 | 24.8 | 39.8 |

TABLE 4

Percent Hard Segment in Compositions
Based on 28,750 M.W. Soft Segment

| | Percent Hard Segment S:H Mole Ratio | | |
|---|---|---|---|
| Value of m | 2 | 1 | 0.5 |
| 0 | 0.2 | 0.3 | 0.5 |
| 1 | 0.7 | 1.5 | 2.9 |
| 2 | 1.3 | 2.6 | 5.1 |
| 3 | 1.9 | 3.7 | 7.2 |
| 4 | 2.5 | 4.8 | 9.2 |
| 5 | 3.0 | 5.9 | 11.1 |
| 6 | 3.6 | 6.9 | 12.9 |
| 7 | 4.1 | 7.9 | 14.7 |
| 10 | 5.7 | 10.8 | 19.5 |
| 14 | 7.8 | 14.4 | 25.2 |
| 24 | 12.5 | 22.3 | 36.5 |
| 28 | 14.3 | 25.1 | 40.1 |

TABLE 5

Percent Hard Segment in Compositions
Based on 33,250 M.W. Soft Segment

| | Percent Hard Segment S:H Mole Ratio | | |
|---|---|---|---|
| Value of m | 2 | 1 | 0.5 |
| 0 | 0.1 | 0.3 | 0.5 |
| 1 | 0.6 | 1.3 | 2.5 |
| 2 | 1.1 | 2.3 | 4.4 |
| 3 | 1.6 | 3.2 | 6.2 |
| 4 | 2.1 | 4.2 | 8.0 |
| 6 | 3.1 | 6.0 | 11.4 |
| 8 | 4.1 | 7.8 | 14.5 |
| 12 | 5.9 | 11.1 | 20.1 |
| 16 | 7.7 | 14.3 | 25.0 |
| 30 | 13.4 | 23.6 | 38.2 |
| 33 | 14.5 | 25.4 | 40.5 |

TABLE 6

Percent Hard Segment in Compositions
Based on 50,500 M.W. Soft Segment

| | Percent Hard Segment S:H Mole Ratio | | |
|---|---|---|---|
| Value of m | 2 | 1 | 0.5 |
| 0 | 0.1 | 0.2 | 0.4 |
| 1 | 0.4 | 0.8 | 1.7 |
| 2 | 0.8 | 1.5 | 3.0 |
| 4 | 1.4 | 2.8 | 5.4 |
| 6 | 2.1 | 4.0 | 7.8 |
| 8 | 2.7 | 5.3 | 10.0 |
| 12 | 4.0 | 7.6 | 14.2 |
| 20 | 6.4 | 12.0 | 21.4 |
| 24 | 7.6 | 14.0 | 24.6 |
| 40 | 11.9 | 21.3 | 35.2 |
| 50 | 14.4 | 25.2 | 40.2 |

To the extent desired, similar calculations can be made for any combination of soft segment or first compound, second and third compounds, value of m, and mole ratio of soft segment to hard segment, thereby enabling one having ordinary skill in the art to readily determine the mole ratios of first, second, and third compounds, and, consequently, the amounts of such materials necessary to prepare a composition coming within the scope of the present invention.

By way of illustration, suppose m is selected to be three; each mole of hard segment then must contain three moles of second compound and four moles of third compound. Suppose further that a mole ratio of soft segment to hard segment of 1.5:1 is selected. Since each mole of soft segment must contain two moles of second compound and one mole of first compound, the 1.5:1 S:H mole ratio requires 3 moles of second compound and 1.5 moles of first compound per mole of hard segment. Consequently, the reaction will require 1.5 moles of first compound, 6 moles of second compound, and four moles of third compound. It then becomes a simple matter to calculate the amounts of each compound required, based on the scale desired and the molecular weights of the compounds to be used. It may be noted at this point that the preferred mole ratio of soft segment to hard segment is about 1. Consequently, the preferred range for m is from 0 to about 24.

From the discussion thus far, it should be apparent that the mole ratio of soft segment to hard segment in the polymeric composition cannot be greater than 2 or less than 0.5. If the reaction mixture S:H mole ratio is outside of this range, there necessarily must be present in the final reaction mixture unreacted soft or hard segment. Such a result comes within the scope of the present invention, but is not preferred since such unreacted segments generally contribute to increased water solubility and decreased absorbence of the final reaction product which typically is not purified to remove unreacted materials and/or unwanted by-products of the reaction.

As a practical matter, the permissible molecular weight ranges of the first compound and the soft segment are essentially the same since the molecular weight of the second compound is relatively small when compared with that of the first compound. Consequently, the same range is used herein for both the first compound and the soft segment as a matter of convenience, it being understood that (1) the range is approximate only and (2) in reality, the range of the soft segment is slightly greater than that of the first compound as a result of the reaction between first compound and second compound.

From the discussion thus far, it should be apparent that $X_1$, $X_2$, and $X_5$ represent the nonfunctional group portions of second compounds and that they typically will be the same since only one second compound usually is employed. Similarly, $X_3$ and $X_4$ represent the nonfunctional group portions of third compounds and $X_3$ and $X_4$ typically will be the same since only one third compound usually is employed. In addition, $Z_1$ and $Z_2$ and $Z_3$ and $Z_4$ represent the functional group portions of the second and third compounds, respectively. Furthermore, $Y_1$ and $Y_2$ and $Y_3$ and $Y_4$ represent linkages which result from the reaction of the functional groups of second compounds with those of the first and third compounds, respectively. Typically, all of such linkages will be the same.

As already stated, the superabsorbent, thermoplastic polymeric composition of the present invention can be prepared by the method which comprises:

(A) reacting a first compound with a second compound at a temperature of from about 50 to about 200 degrees C. for a time sufficient to effect essentially complete reaction; and (B) reacting with the product from step A a third compound at a temperature of from about 80 to about 200 degrees C. for a time sufficient to obtain a melt index of less than about 1,000 g per 10 minutes under the test conditions described hereinafter; in which said first compound is a difunctional poly(oxyethylene) having a weight average molecular weight of from about 5,000 to about 50,000; said second compound is an aliphatic, cycloaliphatic, aromatic, or heterocyclic compound having two functional groups which are reactive with the functional groups of said first compound; the mole ratio of said second compound to said first compound is in the range of from about 2 to about 100; said third compound is an aliphatic, cycloaliphatic, aromatic, heterocyclic, or polymeric compound having two functional groups which are reactive with the functional groups of said second compound; the reaction product of said first compound with said second compound, excluding excess second compound, is from about 86 to about 98 percent by weight of the final composition; and said third compound plus the excess of said second compound are from about 2 to about 14 percent by weight of the final composition.

In the first step of the above method, first compound is reacted with second compound at a temperature in the range of from about 50 to about 200 degrees C. for a time sufficient to effect essentially complete reaction. The reaction temperature preferably will be in the range of from about 80 to about 150 degrees C. and most preferably will be in the range of from about 95 to about 120 degrees C. While reaction time is not critical, typically the reaction time will be in the range of from about 20 minutes to about 3 hours when the reaction is carried out in the most preferred temperature range.

The mole ratio of second compound to first compound should be in the range of from about 2 to about 100. Because the hard segment must be polymeric, a larger excess of second compound relative to first compound is required when the third compound is a monomer; in such cases, the polymeric hard segment is formed in situ. If desired, however, the third compound can be a polymer. All that is required in this case is to provide sufficient second compound to covalently link first compound with third compound to give the composition of the present invention. Thus, when the third compound is a monomer, the preferred mole ratio of second compound to first compound is from about 2.5 to about 50; the most preferred mole ratio is from about 2.5 to about 26. When the third compound is polymeric, the preferred mole ratio of second compound to first compound is from about 2 to about 5.

Preferably, the first compound will have a weight average molecular weight of from about 8,000 to about 50,000, more preferably from about 8,000 to about 30,000, and most preferably from about 8,000 to about 16,000.

As already noted, the first compound most preferably is a poly(oxyethylene) diol. When such a compound is employed, the second compound most preferably is a diisocyanate and the third compound most preferably is a diol. In preferred embodiments, the first compound is a poly(oxyethylene) diol having a weight average molecular weight of from about 8,000 to about 16,000, the second compound is 4,4'-methylenebis(phenylisocyanate), the third compound is 1,4-butanediol, and the percent hard segment in the composition is in the range of from about 3 to about 5 percent by weight of the total composition.

The second step of the method of the present invention involves reacting the product from the first step with a third compound at a temperature of from about 80 to about 200 degrees C. for a time sufficient to obtain a melt flow rate of less than about 1,000 g per 10 minutes. Preferably, the reaction temperature will be from about 90 to about 150 degrees C., and most preferably from about 110 to about 130 degrees C.

Although the use of a solvent usually is not necessary, one or more solvents may be employed in either or both steps, if desired. For example, the use of a solvent may be convenient if the viscosity of the reaction mixture in the first step is too high to allow satisfactory mixing.

In general, any solvent can be used which is not reactive with any of the components of the reaction mixture and in which the reactants are sufficiently soluble. Examples of suitable solvents include, by way of illustration only, aliphatic ketones, such as acetone, methyl ethyl ketone, methyl propyl ketone, and the like; aliphatic esters of the lower aliphatic carboxylic acids, such as ethyl acetate, methyl propionate, butyl acetate, and the like; aliphatic ethers, such as diethyl ether, methyl propyl ether, and the like; aromatic hydrocarbons, such as benzene, toluene, the xylenes, and the like; halogenated aliphatic hydrocarbons, such as methylene chloride and the like; dioxane; tetrahydrofuran; dimethylformamide; N-methylpyrrolidone; and the like. The amount of solvent used is not known to be critical. However, a substantial amount of solvent preferably will not be present in the reaction mixture at the conclusion of the second step.

As already stated, the melt flow rate of the reaction mixture at the end of the second step should be less than about 1,000 g per 10 minutes. The melt flow rate value is for a solvent-free reaction mixture. The target value for the melt flow rate is largely dependent upon the use intended for the resulting composition. For example, if the composition is to be converted into a nonwoven web or fabric, the melt flow rate should be from about 20 to about 500 g per 10 minutes, preferably from about 50 to about 400 g per 10 minutes, and most preferably from about 80 to about 300 g per 10 minutes. On the other hand, if the composition is to be extruded as a film, the melt flow rate of the final reaction mixture probably should be from about 10 to about 30 g per 10 minutes.

The melt flow rate was determined in accordance with a slightly modified version of ASTM Test Method D1238-82, "Standard Test Method for Flow Rates of Thermoplastics by Extrusion Plastometer," using a Model VE 4-78 Extrusion Plastometer (Tinius Olsen Testing Machine Co., Willow Grove, Pa.). The modifications were as follows: (1) the sample was predried at ambient temperature under reduced pressure prior to loading; (2) the piston was not preheated; (3) the sample was loaded in 2-3 minutes; and (4) the loaded sample was preheated for 5 minutes. In every case, a 2.16 kg load was employed and the orifice diameter was 2.0955±0.0051 mm.

Because the compositions of the present invention are thermoplastic, they can be melt processed to give films, fibers, nonwoven webs, molded articles, powders, particles, rods, tubes, and the like. Such compositions are especially useful for the preparation of nonwoven webs by meltblowing and spunbonding processes, such as those described in U.S. Pat. Nos. 3,016,599, 3,755,527, 3,704,198, 3,849,241, 3,341,394, 3,692,618, and 4,340,563. Such compositions also can be used in variations thereof. For example, the compositions can be used to prepare a coformed nonwoven material as described generally in U.S. Pat. No. 4,100,324. Each of the foregoing patents is incorporated herein by reference.

Thus, the formation of fibers from the compositions of the present invention by melt spinning techniques represents the area of greatest interest. As used herein, however, the term "fiber" includes not only fibers which consist solely of a composition of the present invention, but also polycomponent fibers, at least one component of which is a composition of the present invention.

Polycomponent fibers are, of course, well known in the art, the two most common examples being sheath-core fibers and side-by-side bicomponent fibers. By way of illustration, a sheath-core fiber could have a polypropylene core and a sheath of a composition of the present invention. Alternatively, the sheath and core polymers could be two different compositions of the present invention. In the alternative case, the core perhaps would be a higher molecular weight polymer having an absorbency lower than that of the sheath composition. Similar polymer selections also are possible with a side-by-side bicomponent fiber.

Tricomponent, and higher polycomponent, fibers are known. In such cases, one or more of the components can be a composition of the present invention.

Because the compositions of the present invention are particularly well-suited for the formation of nonwoven webs by meltblowing and coforming, such processes are described in some detail hereinafter. However, the preparation of nonwovens by other methods is contemplated and comes within the scope of the present invention. For example, continuous filaments can be produced by melt spinning techniques, collected as a tow, and converted to staple fibers. Nonwovens then can be prepared by carding, air forming, or the like. Variations in the production of the staple fibers, such as false twisting, crimping, and the like, can be practiced, if desired.

Referring now to the drawings where like reference numerals represent like structures or like process steps and, in particular, to FIG. 1 which schematically illustrates an apparatus for forming a superabsorbent thermoplastic web in accordance with the present invention, superabsorbent thermoplastic polymer is supplied in, for example, pellet form to a hopper 10 of an extruder 12. If desired, the polymer in the hopper 10 may be maintained under an inert atmosphere, such as nitrogen.

The temperature of the polymer is elevated within the extruder 12 by a conventional heating arrangement (not shown) to melt the polymer. Pressure is applied to the polymer by the action of a rotating screw (not shown), located within the extruder, to convert the polymer into an extrudable condition. The extrudable polymer then is forwarded by the pressure-applying action of the rotating screw to a meltblowing die 14. The elevated temperature of the extrudable polymer is maintained in the meltblowing die 14 by a conventional heating arrangement (not shown). The die 14 generally extends a distance which is about equal to the width 16 of the nonwoven web 18 which is formed by the process. The combination of elevated temperature and elevated pressure conditions which effect extrusion of the composition will vary over wide ranges. For example, at higher elevated temperatures, lower elevated pressures will result in satisfactory extrusion rates and, at higher elevated pressures of extrusion, lower elevated temperatures will effect satisfactory extrusion rates.

Figure 2:
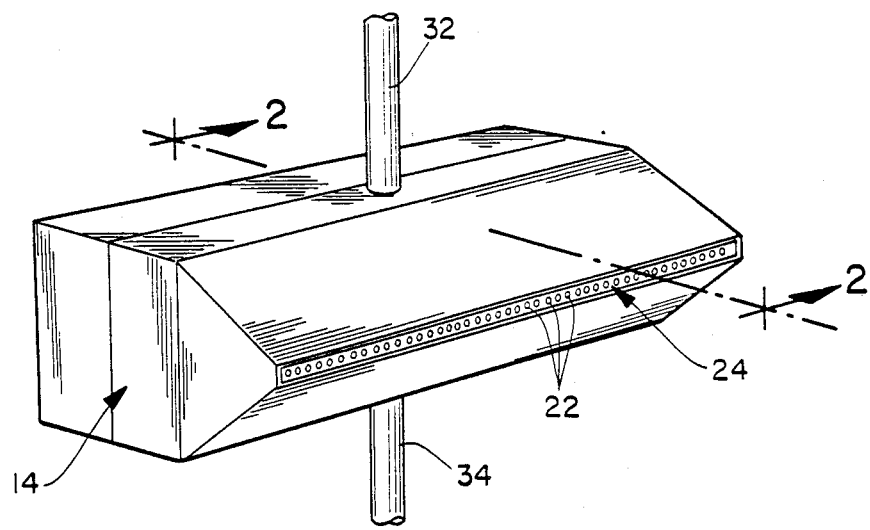
FIG. 2 is a perspective view of the meltblowing die shown in FIG. 1 which illustrates the linear arrangement of the capillaries of the die.

As shown by FIG. 2, the meltblowing die 14 includes an extrusion slot 20 which receives the extrudable polymer from the extruder 12. The extrudable polymer then passes through the extrusion slot 20 (shown in FIGS. 3 and 4) and through a plurality of small diameter capillaries 22 extending across the tip 24 of the die 14 in a linear arrangement, to emerge as molten threads 26 (shown in FIG. 2). Preferably, the polymer is extrudable at pressures of no more than about 300 psig. Typically, such pressures will be in the range of from about 20 to about 250 psig. More typically, such pressures will be in the range of from about 50 to about 250 psig and most typically from about 125 to about 225 psig. Pressures in excess of these values may rupture or break some dies 14. Generally speaking, the extrudable polymer is extruded through the capillaries 22 of the die 14 at a rate of from at least about 0.02 gram per capillary per minute to about 1.7 or more grams per capillary per minute, typically from at least about 0.1 gram per capillary per minute to about 1.25 grams per capillary per minute. A more typical range is from at least about 0.3 gram per capillary per minute to about 1.1 grams per capillary per minute.

Figure 4:
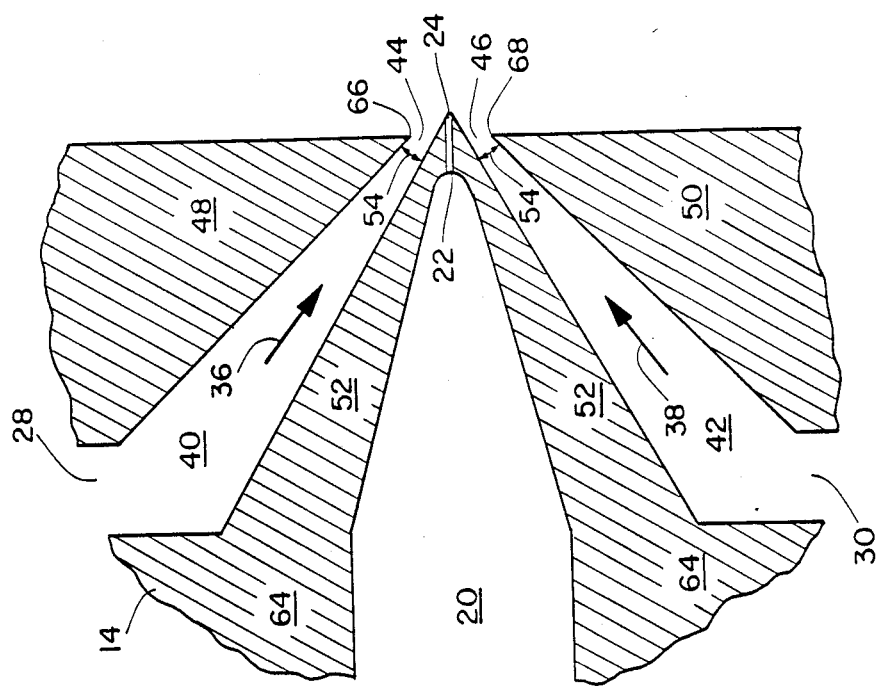
FIG. 4 is a schematic cross-sectional view of the die shown in FIG. 1, along line 2—2 of FIG. 2, illustrating the die in a protruding die tip configuration.
Figure 3:
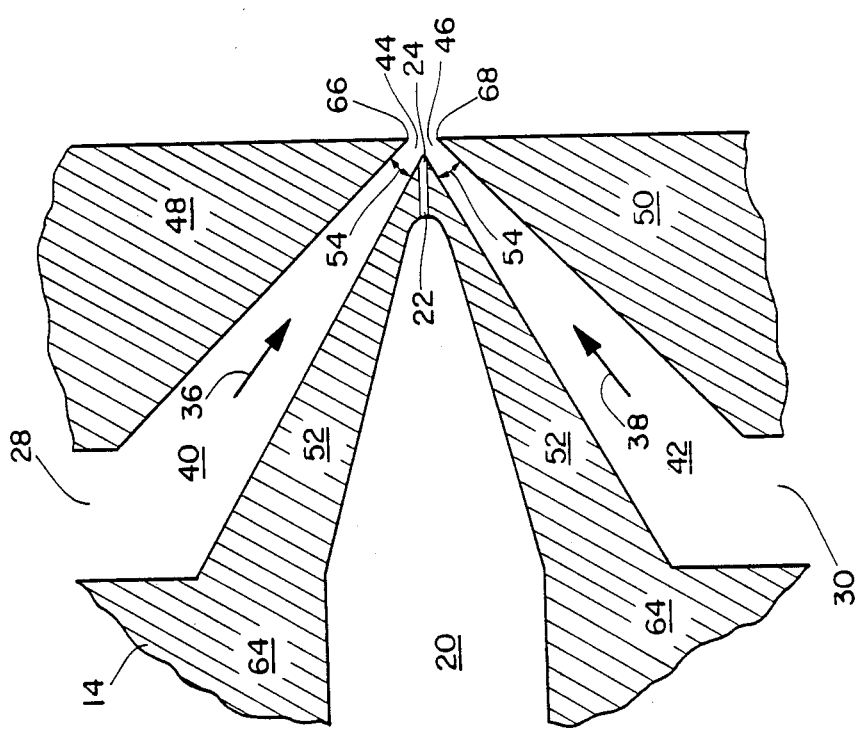
FIG. 3 is a schematic cross-sectional view of the die shown in FIG. 1, along line 2—2 of FIG. 2, illustrating the die in a recessed die tip configuration.

As shown by FIGS. 3 and 4, the die 14 also includes attenuating gas inlets 28 and 30 which are provided with heated, pressurized attenuating gas (not shown) by attenuating gas sources 32 and 34 (shown in FIGS. 1 and 2). The heated, pressurized attenuating gas enters the die 14 at the inlets 28 and 30 and follows the path generally designated by the arrows 36 and 38 through two chambers 40 and 42 and on through to narrow passageways or gaps 44 and 46 so as to contact the extruded threads 26 (shown in FIG. 1) as they exit the capillaries 22 of the die 14. The chambers 40 and 42 are designed in a manner such that the heated attenuating gas exits the chambers 40 and 42 and passes through the gas passages 44 and 46 to form a stream (not shown) of attenuating gas which exits the die 14. The temperature and pressure of the heated stream of attenuating gas can vary widely. For example, the heated attenuating gas can be applied at a temperature of from about 100 to about 250 degrees C. The heated attenuating gas can be applied at a pressure of from about 0.2 to about 20 psig, more specifically from about 0.5 to about 10 psig.

The position of air plates 48 and 50 which, in conjunction with a die-tip portion 52 of the die 14 define the chambers 40 and 42 and the passageways 44 and 46, may be adjusted relative to the die-tip portion 52 to widen or narrow the width 54 of the attenuating gas passageways 44 and 46 so that the volume of attenuating gas passing through the air passageways 44 and 46 during a given time period can be varied without altering the velocity of the attenuating gas. Furthermore, the air plates 48 and 50 can also be adjusted downwardly or upwardly to effect a recessed die-tip configuration or a protruding die-tip configuration, respectively, as discussed in detail below. Generally speaking, it is preferred to utilize attenuating gas pressures of less than about 0.20 psig in conjunction with air passageway widths, which are usually the same, of no greater than about 0.20 inch (about .5 mm). Lower attenuating gas velocities and wider air passageway gaps are generally preferred if substantially continuous fibers are to be produced.

The two streams of attenuating gas converge to form a stream of gas which entrains and attenuates the molten threads 26, as they exit the linearly arranged capillaries 22, into fibers or, depending upon the degree of attenuation, microfibers (also designated 26) of a small diameter, to a diameter less than the diameter of the capillaries 22. The gas-borne fibers 26 are blown, by the action of the attenuating gas, onto a collecting arrangement which, in the embodiment illustrated in FIG. 1, is a foraminous endless belt 56 conventionally driven by rollers 57.

The distance of the collecting arrangement from the die tip (forming distance) must be sufficient to permit at least partial fiber solidification before the fibers contact the collecting arrangement. Furthermore, the fibers must remain on the collecting arrangement for a time sufficient for the resulting nonwoven web to gain sufficient strength or integrity to permit removal of the web from the collecting arrangement. Because the forming distance and the residence time on the collecting arrangement are dependent upon the superabsorbent thermoplastic polymer per se and, at least in part, are interdependent, it is not possible to specify precise ranges for each. However, the selection of forming distance and residence time on the collection arrangement are within the abilities of one having ordinary skill in the art, without the need for undue experimentation.

It should be noted, however, that forming distance and residence time on the collecting arrangement can have only minimal importance, depending upon the circumstances. Such circumstances might include, by way of illustration, forming the nonwoven web on a carrier sheet which serves as a transporting means for the nonwoven web; the use of a coforming process in which the secondary fibers are composed of a composition of the present invention; the use of two or more meltblowing dies in series for the simultaneous production of a nonwoven web which can function as a carrier sheet; the use of one or more meltblowing dies in series with one or more spunbonded or coform dies for the same purpose; and the like.

FIG. 1 illustrates the formation of substantially continuous fibers 26 on the surface of the belt 56. However, the fibers 26 can be formed in a substantially discontinuous fashion by varying the velocity of the attenuating gas, the temperature of the attenuating gas and the volume of attenuating gas passing through the air passageways in a given time period. Other foraminous arrangements such as a drum arrangement may be utilized. The belt 56 also may include one or more vacuum boxes (not shown) located below the surface of the foraminous belt 56 and between the rollers 57. The fibers 26 are collected as a fibrous nonwoven superabsorbent web 18 on the surface of the belt 56 which is rotating as indicated by the arrow 58 in FIG. 1. The vacuum boxes assist in retention of the fibers 26 on the surface of the belt 56. Typically, the tip 24 of the die tip portion 52 of the meltblowing die 14 is from about 4 inches (about 10 cm) to about 30 inches (about 76 cm) from the surface of the foraminous endless belt 56 upon which the fibers 26 are collected. The thus-collected, entangled fibers 26 form a coherent, i.e. cohesive, fibrous nonwoven superabsorbent web 18 which may be removed from the foraminous endless belt 56 by a pair of pinch rollers 60 and 62 which may be designed to press the entangled fibers of the web 18 together to improve the integrity of the web 18. Thereafter, the web 18 may be transported by a conventional arrangement to a wind-up roll (not shown) for storage. Alternatively, the web 18 may be removed directly from the belt 56 by the wind-up roller. The web 18 may be pattern-embossed as by ultrasonic embossing equipment (not shown) or other embossing equipment, such as, for example, the pressure nip formed between a heated calender and anvil roll (not shown).

Referring now to FIG. 3, it can be seen that the meltblowing die 14 includes a base portion 64 and a die tip portion 52 which generally extends centrally from the base portion 64. The centrally located die tip portion 52 is inwardly tapered to a "knife-edge" point which forms the tip 24 of the die tip portion 52 of the die 14. In order to increase the pressures of extrusion which the die 14 can withstand during operation, it is preferred for the base portion 64 and die-tip portion 52 to be formed from a single block of metal which surrounds the extrusion slot 20 and the extrusion capillaries 22. The die 14 also includes two air plates 48 and 50, discussed above, which are secured, by conventional means, to the base portion 64 of the die 14. The air plate 48, in conjunction with the die tip portion 52 of the die 14, defines the chamber 40 and the attenuating gas air passage or gap 44. The air plate 50, in conjunction with the die tip portion 52, defines the chamber 42 and the air passageway or gap 46. Air plate 48 and air plate 50 terminate, respectively, in air plate lip 66 and air plate lip 68. In the configuration illustrated in FIG. 3, the knife-edge point which forms the tip 24 of the die tip portion 52 of the die 14 is recessed inwardly from the plane formed by the air plate lips 66 and 68. This configuration is referred to herein as a recessed die tip configuration and the perpendicular distance between the plane formed by the lips 66 and 68 and the tip 24 of the die tip portion 52 is given in negative numbers or values. If the tip of the die tip portion 52 of the die 14 were configured to protrude outwardly beyond the plane formed by the lips 66 and 68 of the air plates 48 and 50, as illustrated in FIG. 4, such a configuration is referred to herein as a protruding configuration with such perpendicular distance being given in positive numbers or values. The perpendicular distance values were determined in the examples by actual measurements. It should be noted that, unless otherwise stated, the term "air gap or width," as used herein, is the perpendicular, i.e. minimum, width 54 of either of the air passages 44 and 46. These widths are normally arranged to be identical.

Figure 5:
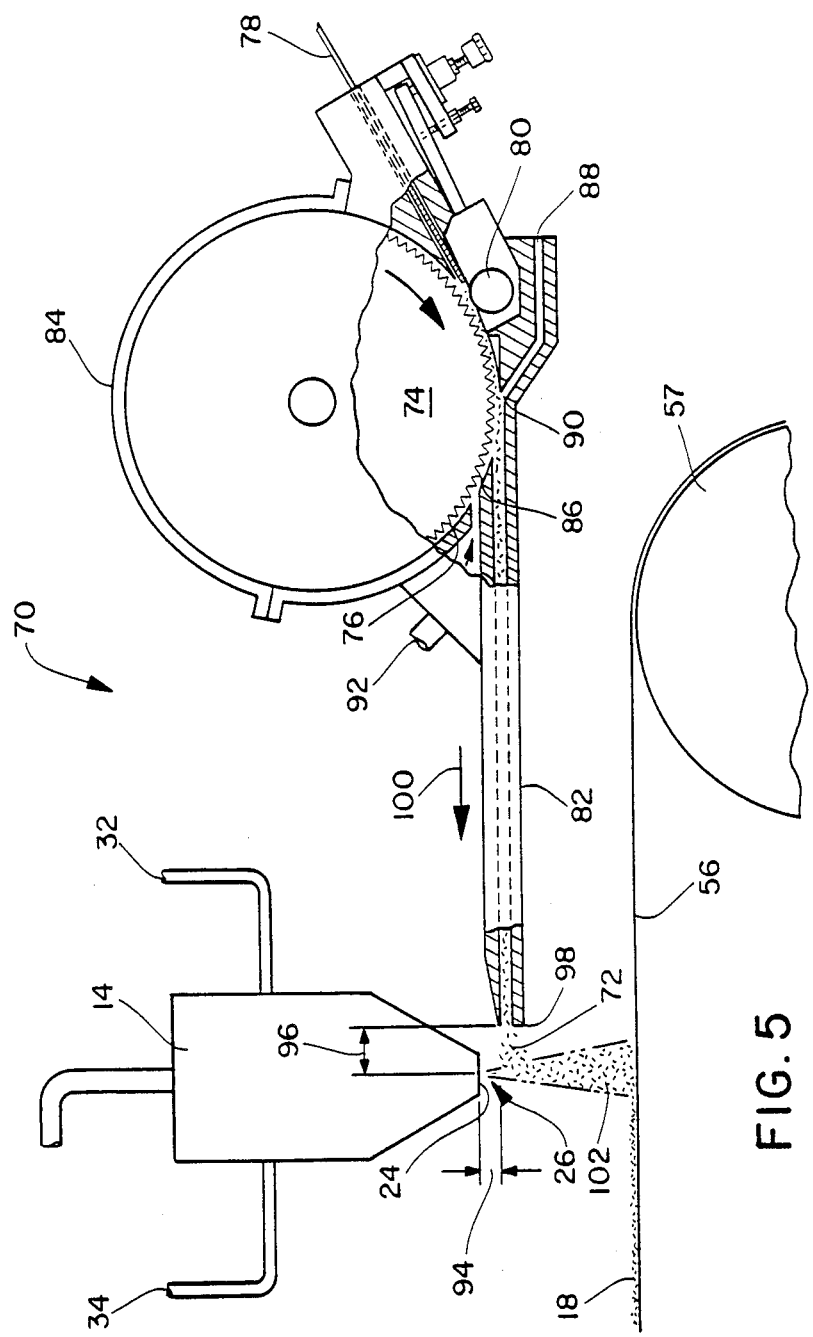
FIG. 5 is a schematic cross-sectional view with portions broken away for purposes of illustration of an arrangement, i.e., a coform process, which may be utilized to incorporate discrete particles, fibers or other materials into the extruded threads of molten material prior to their formation into a nonwoven web.

In some situations it may be desirable to incorporate discreet particles of one or more solid materials into the extruded threads 26 prior to their collection as a nonwoven superabsorbent web 18. For example, it may be desirable to incorporate one or more fibers such as cotton fibers, wood pulp fibers, polyester fibers or other types of fibers or particulates into the threads 26. Blends of two or more of such fibers or particulates can be incorporated. This may be accomplished by utilization of a coforming apparatus such as is illustrated schematically in FIG. 5 at 70. Several types of coforming arrangements are well-known to those in the art and one such arrangement is represented by the apparatus disclosed in U.S. Pat. No. 4,100,432 to Anderson et al. FIG. 5 illustrates that, after formation of the fibers 26, a stream of secondary fibers or particulates 72 is generally uniformly injected into the stream of fibers 26. Distribution of the secondary fibers 72 generally uniformly throughout the stream of fibers 26 preferably is accomplished by merging a secondary gas stream (not shown) containing the secondary fibers 72 with the stream of fibers 26. Apparatus for accomplishing this merger includes a conventional picker roll 74 which has a plurality of teeth 76 that are adapted to separate a matt or batt of secondary fibers 78 into the individual secondary fibers 72. The matt or batt of secondary fibers 78 which is fed to the picker roll 74 may be a sheet of pulp fibers (if a two component mixture of superabsorbent fibers and pulp fibers is desired), a matt or batt of staple fibers (if a two component mixture of superabsorbent fibers and staple fibers is desired) or both a sheet of pulp fibers and a matt or batt of staple fibers (if a three component mixture of superabsorbent fibers, pulp fibers and staple fibers is desired). Other combinations of one or more staple fibers and/or one or more pulp fibers may be utilized. The sheet or matt of secondary fibers 78 is fed to the picker roll 74 by a roller arrangement 80. After the teeth 76 of the picker roll 74 have separated the sheet or matt 78 into separate secondary fibers 72, the individual secondary fibers 72 are conveyed toward the meltblown stream 26 of superabsorbent fibers through a forming duct or nozzle 82. A housing 84 encloses the picker roll 74 and provides a passageway or gap 86 between the housing 84 and the surface of the picker roll 74. A gas (not shown), preferably air, is supplied to the passageway or gap 86 between the surface of the picker roll 74 and the housing 84 by way of a gas duct 88. The gas duct 88 preferably enters the passageway or gap 86 generally at the junction 90 of the forming duct or nozzle 82 and the passageway 86. The gas is supplied in sufficient quantity to serve as a medium for conveying the secondary fibers 72 from the teeth 76 of the picker roll 74 and through the forming duct or nozzle 82 at a velocity approaching that of the teeth 76 of the picker roll 74.

As an aid in maintaining satisfactory secondary fiber 72 velocity, the forming duct or nozzle 82 is desirably positioned so that its longitudinal axis is substantially parallel to a plane which is tangential to the surface of the picker roll 74 at the junction 90 of the forming duct or nozzle 82 with the gap 86. As a result of this arrangement, the velocity of the secondary fibers 72 is not substantially changed by contact of the secondary fibers 72 with the walls of the forming duct or nozzle 82. If the secondary fibers 72 remain in contact with the teeth 76 of the picker roll 74 after they have been separated from the matt or sheet 78, the axis of the forming duct or nozzle 82 may be adjusted appropriately to be aligned in the direction of secondary fiber 72 velocity at the point where the secondary fibers 72 disengage from the teeth 76 of the picker roll 74. If desired, the disengagement of the secondary fibers 72 with the teeth 76 of the picker roll 74 may be assisted by application of a pressurized gas, i.e., air, through duct 92.

The height 94 of the forming duct or nozzle 82 with respect to the die tip 24 may be adjusted to vary the properties of the coformed product. Variation of the distance 96 of the tip 98 of the nozzle 82 from the die tip 24 will also achieve variations in the final coformed product. The height 94 and distance 96 values will also vary with the material being added to the fibers 26. The width of the forming duct or nozzle 82 along the picker roll 74 and the length 100 that the forming duct or nozzle 82 extends from the picker roll 74 are also important in obtaining optimum distribution of the secondary fibers 72 throughout the stream of meltblown fibers 26. Preferably, the length 100 of the forming duct or nozzle 82 should be as short as equipment design will allow. The length 100 is usually limited to a minimum length which is generally equal to the radius of the picker roll 74. Preferably, the width of the forming duct or nozzle 82 should not exceed the width of the sheets or matts 78 that are being fed to the picker roll 74.

FIG. 5 further illustrates that the gas stream carrying the secondary fibers 72 is preferably moving in a direction which is generally perpendicular to the direction of movement of the stream of the fibers 26 at the point of merger of the two gas streams. Other angles of merger of the two streams may be utilized. The velocity of the gas stream carrying the secondary fibers 72 is usually adjusted so that it is less than the velocity of the gas stream which attenuates the fibers 26. This allows the streams, upon merger and integration thereof, to flow in substantially the same direction as that of the stream of fibers 26. Indeed, the merger of the two streams is preferably accomplished in a manner which is somewhat like an aspirating effect whereby the stream of secondary fibers 72 is drawn into the stream of fibers 26. It is also preferred that the velocity difference between the two gas streams be such that the secondary fibers 72 are integrated into the fibers 26 in a turbulent manner so that the secondary fibers 72 become thoroughly mixed with the fibers 26. In general, increasing the velocity differential between the two streams produces a more homogeneous integration of the secondary fibers 72 into the fibers 26 and decreases in the velocity differential between the two streams are generally expected to produce concentrated areas of secondary fibers 72 within the fibers 26. Generally, for increased production rates it is preferred for the gas stream which entrains and attenuates the stream of fibers 26 to have an initially high velocity, for example from about 200 to about 1,000 feet per second, and for the stream of gas which carries the secondary fibers 72 to have an initially low velocity, for example from about 50 to about 200 feet per second. Of course, after the stream of gas which entrains and attenuates the extruded threads 26 into superabsorbent fibers exits the air passageways 44 and 46 of the meltblowing die 14, it immediately expands and decreases in velocity.

Upon merger and integration of the stream of secondary fibers 72 into the stream of fibers 26 to generally uniformly distribute the secondary fibers 72 throughout the stream of meltblown fibers 26, as discussed above, a composite stream 102 of fibers 26 and secondary fibers 72 is formed. The fibers 26 may still be semi-molten and tacky at the time of incorporation of the secondary fibers 72 into the fibers 26, and, in such a situation, the secondary fibers 72 are not only mechanically entangled within the fibers 26 but also usually become thermally bonded thereto. However, if the fibers 26 are not semi-molten and tacky at the time of incorporation of the secondary fibers 72 therein, the secondary fibers 72 will only be mechanically entangled within the fibers 26.

In order to convert the composite stream 102 of fibers 26 and secondary fibers 72 into a fibrous nonwoven web 18 of fibers 26 having the secondary fibers 72 generally uniformly distributed throughout and, if desired, bonded to the fibers 26 of the web 18, a collecting device is located in the path of the composite stream 102. The collecting device may be a rotating belt 56 as described with respect to FIG. 1 upon which the composite stream 102 impacts to form the web 18. Preferably, the external surface of the rotating belt is porous and the rotating belt includes a conventional vacuum arrangement (not shown) which assists in retaining the composite stream 102 on the external surface of the belt. Other collecting devices are well-known to those of skill in the art and may be utilized in place of rotating belt 56; for example, a porous rotating drum arrangement could be utilized. Thereafter, the web 18 may be removed from the belt 56 by a pair of nip rollers (not shown) in an arrangement equivalent to that illustrated in FIG. 1. Thereafter, the web 18. may be transported by a conventional arrangement to a wind-up roller (not shown) for storage. Alternatively, the web 18 may be removed directly from the belt 56 by the wind-up roller.

Depending on the characteristics desired of the coformed fibrous nonwoven superabsorbent web, the web can include (1) from at least about 20 percent by weight of fibers as defined herein, and (2) from greater than 0 percent by weight to about 80 percent by weight of at least one secondary fiber generally uniformly distributed throughout the fibrous nonwoven superabsorbent web. As noted earlier, however, the secondary fibers can be composed of a composition of the present invention, with the fibers 26 being composed of, for example, a polyolefin such as polyethylene and polypropylene, or other suitable thermoplastic polymer.

The picker roll 74 may be replaced by a conventional particulate injection system to make a fibrous nonwoven web 18 containing various particulates. A combination of both coformed fibers and particulates could be added to the fibers 26 prior to their formation into a fibrous nonwoven superabsorbent web 18.

The present invention is further described by the following examples which illustrate specific embodiments. Such examples are not to be construed as in any way limiting either the spirit or scope of the present invention. In the examples, all temperatures are in degrees Celsius and all amounts are in parts by weight, unless specified otherwise. In every case, the poly(oxyethylene) diol was dried overnight at 95 degrees C. under reduced pressure in order to reduce water content to 0.01 percent by weight or less and the assembled resin kettle was heat-dried by passing a portable butane burner flame over the external kettle surfaces while purging the vessel with nitrogen.

EXAMPLE 1

A 500-ml, wide mouth, two piece resin kettle with ground glass flanges and a four-necked cover was charged with 203 g (0.025 mole) of a poly(oxyethylene) diol having a molecular weight of 8,000 (CARBOWAX® PEG-8,000, Union Carbide Corporation, South Charleston, W. Va.) and 19.5 g (0.078 mole) of 4,4'-methylenebis(phenylisocyanate) (Eastman Kodak Co., Rochester, N.Y.). The cover was attached and fitted with a nitrogen inlet, thermometer, condenser, and high torque mechanical stirrer (Caframa, Type RZR50, CSA® Wiarton, Ontario, Canada; Fisher Catalog No. 14-500, Fisher Scientific, Pittsburgh, Pa.). The kettle was flushed with nitrogen and maintained under a nitrogen atmosphere. The reaction mixture was heated to 100 degrees over a one-hour period and maintained at that temperature with stirring for one hour. The kettle then was charged with 4.8 g (0.053 mole) of 1,4-butanediol (J. T. Baker Chemical Co., Phillipsburg, N.J.). Stirring and heating at 100 degrees were continued for about 15 iinutes, during which time the viscosity of the reaction mixture increased to the point where the mixture began to climb up the shaft of the stirrer. The reaction mixture was cooled, removed from the kettle, and stored.

The resulting composition consisted of 94.8 percent by weight soft segment and 5.2 percent by weight hard segment, calculated as follows: from formula (2), it is seen that the weight of soft segment is approximately equal to the amount of first compound or poly(oxyethylene) diol plus an amount of second compound or diisocyanate which is equal to twice the molar amount of first compound. The remaining amount of second compound plus third compound or 1,4-butanediol constitutes the weight of hard segment. Since 0.025 mole of first compound was employed, the weight of second compound which must be added to the weight of first compound is 0.05 mole×250 g/mole or 12.5 g. Thus, the weight of soft segment is 203 g plus 12.5 g, or 215.5 g, while the weight of the composition must equal the sum of the weights of the components, or 227.3 g. Consequently, the percent of soft segment present in the composition is equal to (215.5×100)/227.3, or 94.8 percent. The remainder, of course, is hard segment.

EXAMPLE 2

The procedure of Example 1 was repeated, except that the second stage or step B reaction time was 240 minutes. The final reaction mixture viscosity was comparable to that of Example 1. As with Example 1; the composition consisted of 94.8 percent by weight soft segment and 5.2 percent by weight hard segment.

EXAMPLE 3

The procedure of Example 1 was repeated, except that the initial kettle charge consisted of 214 g (0.015 mole) of a poly(oxyethylene) diol having a molecular weight of 14,000 (CARBOWAX ® PEG-14,000, Union Carbide Corporation, South Charleston, W. Va. and 10.5 g (0.042 mole) of the diisocyanate, the amount of 1,4-butanediol was 2.43 g (0.027 mole), and the second stage or step B reaction time was 83 minutes. The composition obtained consisted of 97.3 percent by weight soft segment and 2.7 percent by weight hard segment.

EXAMPLE 4

The procedure of Example 3 was repeated, except that the amount of the poly(oxyethylene) diol was decreased slightly to 196 g (0.014 mole), the amount of diisocyanate was increased to 14.5 g (0.058 mole), the amount of 1,4-butanediol was increased to 4.21 g (0.044 mole), and the second stage or step B reaction time was 96 minutes. The composition thus obtained consisted of 94.7 percent by weight soft segment and 5.3 percent by weight hard segment.

EXAMPLE 5

The procedure of Example 3 was repeated eleven times, except that a 2-1 resin kettle was employed, and the amounts of poly(oxyethylene) diol, diisocyanate, and 1,4-butanediol were increased four-fold to 857 g (0.061 mole), 42 g (0.168 mole), and 9.6 g (0.107 mole), respectively. In addition, the second stage or step B reaction was continued until the torque on the stirrer reached about 3.2 lb-in, at which time 10.5 g (0.14 mole) of n-butanol was added as a molecular weight limiter. The eleven batches were labeled 5A-5K, respectively As with Example 3, the compositions consisted of 97.3 percent by weight soft segment and 2.7 percent by weight hard segment.

Because higher molecular weight poly(oxyethylene) diols were not available in sufficiently pure form, lower molecular weight poly(oxyethylene) diols were coupled by means of urethane linkages, the extent of coupling being controlled by the ratio of diol and diisocyanate. The coupling reaction in effect yields a soft segment. Consequently, the preparation of the final superabsorbent thermoplastic composition requires the addition of both second compound and third compound for the second stage or step B reaction. This coupling reaction and the subsequent formation of the final composition are illustrated by Examples 6-9, inclusive.

EXAMPLE 6

A 500-ml, wide mouth, two piece resin kettle with ground glass flanges and a four-necked cover was charged with 211 g (0.0264 mole) of the poly(oxyethylene) diol employed in Example 1 and 9.9 g (0.0396 mole) of 4,4'-methylenebis(phenylisocyanate) (a 3:2 mole ratio of diisocyanate to PEG). The cover was attached and fitted as described in Example 1. The kettle was flushed with nitrogen and maintained under a nitrogen atmosphere. The reaction mixture was heated to 100 degrees over a one-hour period and maintained at that temperature with stirring for one hour. The kettle then was charged with an additional 3.3 g (0.0132 mole) of the diisocyanate and 2.4 g (0.0266 mole) of 1,4-butanediol. Stirring and heating at 100 degrees were continued for about 134 minutes, during which time the viscosity of the reaction mixture increased to the point where the mixture began to climb up the shaft of the stirrer. The reaction mixture was cooled, removed from the kettle, and stored. The resulting composition consisted of 97.5 percent by weight soft segment and 2.5 percent by weight hard segment.

The modified poly(oxyethylene) diol obtained from the first stage or step A reaction, before carrying out the next step, was composed of two molecules of the poly(oxyethylene) diol linked together by the diisocyanate. Such modified poly(oxyethylene) diol can be represented schematically as follows: MDI-PEG-MDI-PEG-MDI in which MDI represents the diisocyanate and PEG represents the poly(oxyethylene) diol. Such modified poly(oxyethylene) diol or soft segment had a molecular weight of about 16,750.

EXAMPLE 7

The procedure of Example 6 was repeated two times, except that in each case a 2-1 resin kettle was employed, the initial kettle charge consisted of 845 g (0.106 mole) of poly(oxyethylene) diol and 39.6 g (0.158 mole) of diisocyanate (a 3:2 mole ratio of diisocyanate to PEG), the subsequent kettle charge consisted of 13.2 g (0.053 mole) of diisocyanate and 9.6 g (0.107 mole) of 1,4-butanediol, and the second stage or step B reaction times for the two procedures were 113 minutes and 159 minutes, respectively. The two batches of polymers were labeled 7A and 7B, respectively. As with Example 6, the compositions consisted of 97.5 percent by weight soft segment and 2.5 percent by weight hard segment.

EXAMPLE 8

The procedure of Example 6 was repeated, except that the initial kettle charge consisted of 240 g (0.017 mole) of the poly(oxyethylene) diol employed in Example 6 and 6.4 g (0.026 mole) of the diisocyanate (a 3:2 mole ratio of diisocyanate to PEG), the subsequent kettle charge consisted of 5.3 g (0.021 mole) of the diisocyanate and 2.7 g (0.030 mole) of 1,4-butanediol, and the second stage or step B reaction time was 124 minutes. The resulting composition consisted of 96.8 percent by weight soft segment and 3.2 percent by weight hard segment.

The modified poly(oxyethylene) diol obtained from the first stage or step A reaction was composed of two molecules of the poly(oxyethylene) diol linked together by the diisocyanate. Such modified poly(oxyethylene) diol can be represented schematically as follows: MDI-PEG-MDI-PEG-MDI. Such modified poly(oxyethylene) diol or soft segment had a molecular weight of about 28,750.

EXAMPLE 9

The procedure of Example 6 was repeated, except the initial kettle charge consisted of 211 g (0.026 mole) of the poly(oxyethylene) diol employed in Example 3 and 8.3 g (0.033 mole) of the diisocyanate (a 5:4 mole ratio of diisocyanate to PEG), the subsequent kettle charge consisted of 5.0 g (0.020 mole) of the diisocyanate and 2.4 g (0.027 mole) of 1,4-butanediol, and the second stage or step B reaction time was 200 minutes. The resulting composition consisted of 96.8 percent by weight soft segment and 3.2 percent by weight hard segment.

The modified poly(oxyethylene) diol obtained from the first stage or step A reaction was composed of four molecules of the poly(oxyethylene) diol linked together by the diisocyanate. Such modified poly(oxyethylene) diol can be represented schematically as follows: MDI-PEG-MDI-PEG-MDI-PEG-MDI-PEG-MDI. Such modified poly(oxyethylene) diol or soft segment had a molecular weight of about 33,250.

As already noted, Examples 6-9, inclusive, detail the preparation of soft segment followed by the in situ preparation of hard segment with the concomitant formation of the desired composition. It is possible, of course, to prepare both the soft and hard segments separately and then combine them to obtain a superabsorbent thermoplastic composition. This procedure is illustrated by Example 10.

EXAMPLE 10

Preparation of Hard Segment

A 50-ml, wide mouth, two piece resin kettle with ground glass flanges and a three-necked cover was charged with 9.96 g (0.1107 mole) of 1,4-butanediol (J. T. Baker Chemical Co., Phillipsburg, N.J.) and 13.83 g (0.0553 mole) of 4,4'-methylenebis(phenylisocyanate) (Eastman Kodak Co., Rochester, N.Y.). The cover was attached and fitted with a nitrogen inlet, condenser, and mechanical stirrer (T-line Laboratory Stirrer, Model No. 134-2, Talboys Engineering Corp., Emerson, N.J.). The kettle was flushed with nitrogen and maintained under a nitrogen atmosphere. The reaction mixture was heated in an oil bath to 72 degrees over ten minutes, after which a solid material formed. The resulting hard segment melted over the range 175-185 degrees.

The hard segment was characterized by hydroxyl number in order to estimate the molecular weight of the hard segment, or the extent of coupling of diol to diisocyanate. The hydroxyl number, which is defined as the number of milligrams of potassium hydroxide equivalent to the hydroxyl content of 1 g of sample, was determined as follows: Duplicate approximately 1.5 g samples were weighed into tared single-necked round-bottomed flasks. To each flask was added exactly 25 ml of phthalating reagent which consisted of 42.0 g of phthalic anhydride in 300 ml of freshly distilled pyridine. Each flask was fitted with a condenser and purged slowly with nitrogen. The flasks were placed in an oil bath at 115 degrees for one hour. Using five drops of phenolphthalein solution as the indicator, the reaction solution of each flask was titrated while hot with 0.5N aqueous sodium hydroxide to a faint pink end-point lasting for 15 seconds. Blank samples were run with only the phthalating reagent. The hydroxyl number then was calculated by dividing the milliequivalents of potassium hydroxide required (corrected for the blank) by the weight of the sample. The average hydroxyl number from the duplicate runs was 270. This number is equivalent to an apparent molecular weight for the hard segment of 416. Since the theoretical hard segment molecular weight is 430, the hydroxyl number indicates that there probably was a slight excess of 1,4-butanediol present in the hard segment reaction mixture.

Preparation of Soft Segment

A 500-ml, wide mouth, two piece resin kettle with ground glass flanges and a four-necked cover was charged with 391.5 g (0.028 mole) of the poly(oxyethylene) diol and 13.98 g (0.056 mole) of the diisocyanate employed in Example 3. The cover was attached and fitted with a nitrogen inlet, thermometer, condenser, and high torque mechanical stirrer (Caframa, Type RZR50, CSA ®, Wiarton, Ontario, Canada; Fisher Catalog No. 14-500, Fisher Scientific, Pittsburgh, Pa.). The kettle was flushed with nitrogen and maintained under a nitrogen atmosphere. The reaction mixture was heated to 100 degrees over a one-hour period and maintained at that temperature with stirring for 231 minutes.

Preparation of Superabsorbent Thermoplastic Composition

To the resulting soft segment was added 11.63 g (0.027 mole) of hard segment dissolved in about 40 ml of dry N-methyl-2-pyrrolidinone. The resulting mixture was heated at 72-82 degrees for 158 minutes to give the desired composition, the last 15 minutes being under reduced pressure to remove the solvent. The resulting composition consisted of 97.2 percent soft segment and 2.8 percent hard segment.

The compositions prepared in the preceding examples all are polyether urethanes based on a poly(oxyethylene) diol and an aliphatic third compound, 1,4-butanediol. Moreover, in cases where the poly(oxyethylene) diol was coupled to give a modified poly(oxyethylene) diol leading to a higher molecular weight soft segment, coupling employed a diisocyanate which resulted in the formation of urethane bonds. Consequently, all of such compositions contain only ether and urethane linkages.

As already stated, however, the compositions of the present invention are not limited to aliphatic third compounds or only to ether and urethane linkages, as demonstrated by the next five examples.

EXAMPLE 11

Preparation of Polyether Urethane Ester

Following the procedure of Example 1, the resin kettle was charged with 212.8 g (0.0266 mole) of the poly(oxyethylene) diol employed in Example 1. As the diol was being heated to 95 degrees, 2.70 g (0.0133 mole) of terephthaloyl chloride (recrystallized from hexane) was added to the resin kettle. Unlike the use of a diisocyanate as a coupling agent, the use of terephthaloyl chloride does not result in the formation of soft segment. The resulting reaction mixture was heated, with stirring and under a nitrogen atmosphere, at 95 degrees for about 1.5 hours. To the kettle then was added 10.0 g (0.040 mole) of the diisocyanate employed in Example 1; the temperature of the reactio mixture now was 104 degrees. After an additional hour, 2.40 g (0.0267 mole) of 1,4-butanediol was added. The reaction mixture was heated for one more hour, at which time 2.0 g (0.027 mole) of n-butanol was added as described in Example 5. The resulting composition contained 97.5 percent soft segment and 2.5 percent hard segment.

EXAMPLE 12

Use of a Third Compound Containing an Aromatic Group

The procedure of Example 1 was repeated, except that the initial kettle charge consisted of 305.6 g (0.0382 mole) of the poly(oxyethylene) diol and 19.1 g (0.0764 mole) of the diisocyanate, in the second stage reaction the 1,4-butanediol was replaced with 7.56 g (0.038 mole) of hydroquinone bis(2-hydroxyethyl) ether (Eastman Kodak Co., Kingsport, Tennessee), and the second state or step B reaction time was 47 minutes. It may be noted that the first compound: second compound: third compound mole ratio was 1:2:1. The resulting composition contained 97.7 percent soft segment and 2.3 percent hard segment.

EXAMPLE 13

In order to evaluate the effect of replacing the third compound used in Example 12 with the aliphatic diol employed in Examples 1–10, inclusive, the procedure of Example 12 was repeated with the same 1:2:1 mole ratio of first compound: second compound: third compound. Thus, the initial kettle charge consisted of 208 g (0.026 mole) of the poly(oxyethylene) diol and 13.25 g (0.053 mole) of diisocyanate, the amount of 1,4-butanediol was 2.34 g (0.026 mole), and the second stage or step B reaction time was 280 minutes. The resulting composition consisted of 98.8 percent soft segment and 1.2 percent hard segment. The decrease in the percent hard segment relative to the composition of Example 12 is a result of the lower molecular weight of 1,4-butanediol.

EXAMPLE 14

Preparation of Polyether Urethane Amide

Following the procedure of Example 11, the resin kettle was charged with 63.81 g (0.00798 mole) of the poly(oxyethylene) diol employed in Example 1 and 250 ml of dry N-methyl-2-pyrrolidinone. As the reaction mixture was being heated and after the diol had dissolved, 3.99 g (0.01596 mole) of the diisocyanate employed in Example 1 was added to the kettle. The reaction solution was heated at 65 degrees for one hour. To the resin kettle then were added 1.17 g (0.00798 mole) of adipic acid, 100 ml of N-methyl-2-pyrrolidinone, and a catalytic amount of sodium hydride. The resulting solution was heated at 120 degrees for one hour. Films were cast from the reaction solution and air dried, followed by drying under reduced pressure at 80 degrees. The composition consisted of 98.3 percent soft segment and 1.7 percent hard segment.

EXAMPLE 15

Preparation of Polyether Urethane Amide

Following the procedure of Example 14, the resin kettle was charged with 45.02 g (0.0032 mole) of the poly(oxyethylene) diol of Example 3, 4.89 g (0.0196 mole) of the diisocyanate, and 300 ml of dry N-methyl-2-pyrrolidinone. The reaction mixture was heated to 100 degrees over a one-half hour period and maintained at that temperature for 1.5 hours. To the kettle then were added 2.40 g (0.016 mole) of adipic acid and a catalytic amount of sodium hydride. Heating was continued for an additional hour. The composition consisted of 89.1 percent soft segment and 10.9 percent hard segment.

The next example briefly summarizes scale-up activities with respect to certain of the compositions prepared in the preceding examples.

EXAMPLE 16

The procedure of Example 6 was repeated a number of times in 50-lb. and 200-lb. batches using appropriate multiples of reactants. The second step reaction was carried out for four hours at 130 ±30 degrees. In each case, zinc octoate was added with the 1,4-butanediol at a level of 8 g zinc octoate per 1,000 lbs. of polymer. Each composition, of course, consisted of 97.5 percent by weight soft segment and 2.5 percent by weight hard segment.

The compositions obtained in the above examples were characterized by a number of methods:

1. Infrared analysis (IR). A sample of the composition was mulled in Nujol. The instrument was a Perkin-Elmer Model 710B Spectrophotometer (Perkin-Elmer Corporation, Norwalk, Conn.).

2. Proton nuclear magnetic resonance analysis (NMR). The sample was dissolved in chloroform at a concentration of 10 percent by weight. The instrument was an IBM Instruments Model NR/250AF 250 Megahertz Spectrophotometer (IBM Corporation, Armonk, N.Y.).

3. Elemental analysis (EA). Elemental analyses were carried out by Atlantic Microlabs, Atlanta, Ga.

4. Inherent viscosity (IV). The apparatus employed was a Schotte Gerate KPG ® Ubbelohde Viscometer (Jenaer Glasswerk Schott & Gen., Mainz, Germany) with a suspended level bulb. The sample was dissolved in m-cresol at a concentration of 0.5 percent, weight per volume. The solution was filtered through a medium frit scintered glass funnel and equilibrated 30 min at 30 degrees in a constant temperature bath (Canner Instrument Company, Boalsburg, Pa.) before measuring the rate of flow.

5. Melting point (MP). The melting point range of the sample was determined by means of a hotbench (C. Reichert Ag., Wien, Austria).

6. Melt flow rate (MFR). The melt flow rate was determined as described at page 31.

7. Tensile strength (TS) (Ultimate Modulus). Tensile strength was measured on film samples by means of an Instron Model 1122 (Instron Corporation, Canton, Mass.). Films were made in a Carver Laboratory Press, Model 2518 (Fred S. Carver, Inc., Menomonee Falls, Wis.) at 175 degrees and a pressure less than 100 pounds, the minimum gauge pressure reading. Since roughly 5 g of polymer was employed in each case and film thickness varied from 0.010 to 0.031 inch (0.25 to 0.79 mm), the estimated pressure range was from about 2 to about 10 psi. The films were equilibrated at ambient temperature and humidity for at least one day. Rectangular film samples measuring 0.5×1.5 inch (12.7×38.1 mm) were cut from the films. The ends of the samples were wrapped with masking tape. The Instron grips had 1×1.5 inch (25.4×38.1 mm) smooth rubber faces. Gauge length was one inch (25.4 mm) and the crosshead speed was 2 inches (50.8 mm) per minute.

8. Thermal gravimetric analysis (TGA). Thermal gravimetric analysis employed a DuPont Model 1090 Thermal Analyzer with a Model 1091 Disc Memory and a Model 950 Thermal Gravimetric Analyzer (DuPont Instruments, Wilmington, Del.). Each polymer sample (8-10 mg) was weighed in a tared platinum sample pan and heated to 550 degrees at 10 degrees/minute.

9. Differential scanning calorimetry (DSC). Each polymer was analyzed by differential scanning calorimetry using a DuPont Model 1090 Thermal Analyzer with a Model 1091 Disc Memory and a Model 910 Differential Scanning Calorimeter (DuPont Instruments, Wilmington, Del.). Polymer (about 4 mg) was weighed in a tared, non-hermetically sealed aluminum pan and cooled in the sample cell to −80 degrees with a liquid nitrogen jacket. The sample then was heated at 10 degrees/minute to 550 degrees.

10. Centrifuge Absorbency (A) and Solubility (S). Absorbency was determined with either water (WA) or with synthetic urine (SUA). Briefly, a polymer sample was melt-pressed into a film essentially as described above in method 7 (tensile strength). A film thickness of 0.0109 inch (0.28 mm) was achieved by using flat metal spacer strips and TEFLON ®-coated foil. The film was cut into 1-cm squares which were weighed. Each square was placed in water or synthetic urine at ambient temperature and allowed to soak for four hours. The soaked sample was placed in a centrifuge tube adapter. The adapter had at the bottom a barrier to the sample which was permeable to the test liquid under the conditions of centrifugation. The sample then was centrifuged at 1,000 rpm (196 x G) for 30 minutes. To the extent possible, the sample was removed from the centrifuge tube adapter and placed in a tared aluminum weighing dish. The sample was weighed, dried for three hours at 90 degrees, and reweighed. The absorbency then was calculated in accordance with the following equation $$A = (\text{wt. wet} - \text{final wt. dry})/\text{final wt. dry}$$

Thus, absorbency is the number of g of test liquid absorbed per g of sample, corrected for soluble sample. When synthetic urine was used, the final dry weight also was corrected for the solids present in the absorbed liquid.

The solubility of the test sample, expressed as a percentage, was calculated from the water absorbency data as follows:

$$S = 100(\text{initial wt. dry} - \text{final wt. dry})/\text{initial wt. dry}$$

The synthetic urine test liquid contained the following compounds in the amounts shown, per liter of liquid:

0.309 g of $Ca(H_2PO_4)_2 \cdot H_2O$
0.681 g of $KH_2PO_4$
0.477 g of $MgSO_4 \cdot 7H_2O$
1.333 g of $K_2SO_4$
1.244 g of $Na_3PO_4 \cdot 12H_2O$
4.441 g of $NaCl$
3.161 g of $KCl$
0.400 g of $NaN_3$
8.560 g of urea The compounds were added in the order listed to 900 ml of distilled water in a well rinsed, chromic acid washed, 1000 ml volumetric flask; each compound was dissolved completely before the next one was added. Distilled water then was added to the mark. The total solids content of the synthetic urine was 20.606 g/liter which is approximately equivalent to 2.01 percent by weight.

The IR and NMR analyses supported the structures described herein for the compositions of the present invention, as did the EA. The MP determinations gave broad ranges which were indicative of wide molecular weight distributions. The thermograms obtained by DSC showed endotherms at about 50-60 degrees and 410-430 degrees, indicating the presence of block copolymers. Finally, TGA demonstrated that the compositions are stable, at least in a nitrogen atmosphere, to about 260 degrees, in that they undergo less than one percent by weight degradation. Some of the other characterization results are summarized in Table 7; it perhaps should be noted that the preferred temperature for determining the melt flow rate is 195 degrees.

TABLE 7
Summary of Melt Flow Rates and Absorbencies

| Example | Absorbency, g/g Water | Absorbency, g/g Syn. Urine | Water Sol.[a] | Melt Flow Rate/Temp. |
|---|---|---|---|---|
| 1 | — | — | — | — |
| 2 | 14.2 | 12.2 | 23 | 300/190° |
| 3 | 40.7 | 44 | 38 | 65/140° |
| 4 | 39.2 | 48.2 | 45 | 294/190° |
| 5A | — | — | — | 33/195° |
| 5B | — | — | — | 16/195° |
| 5C | — | — | — | 20/195° |
| 5D | — | — | — | 47/195° |
| 5E | — | — | — | 27/195° |
| 5F | — | — | — | 48/195° |
| 5G | — | — | — | 63/195° |
| 5H | 41.9 | 31.7 | — | 103/195° |
| 5I | — | — | — | 30/195° |
| 5J | — | — | — | 130/195° |
| 5K | — | — | — | 122/190° |
| 6 | 33.7 | 27.7 | 27 | 90/195° |
| 7A | — | — | — | 64/195° |
| 7B | — | — | — | 300/195° |
| 8 | 39.2 | 31 | 43 | 116/195° |
| 9 | 50.6 | 41.3 | 49 | 119/190° |
| 10 | 20.7 | 19.4 | 28.5 | — |
| 11 | 10.7[b] | 11.5[b] | — | 200/190° |
| 12 | 17.7 | 14.6 | 36.2 | 91/190° |
| 13 | Diss. | Diss. | — | 182/190° |
| 14 | 74.7 | Diss. | — | — |
| 15 | 31.3 | 72.8 | — | — |
| 16 | — | — | — | 43-147/190°[c] |

[a] Percent of sample soluble in water at ambient temperature.
[b] Measured with 0.5 cm or smaller chips of polymer which were soaked for approximately 24 hours.
[c] Range of values obtained for multiple batches.

Finally, the inherent viscosity and ultimate modulus were determined for each of the polymers of Examples 3 and 4. The values obtained are summarized in Table 8.

TABLE 8
Summary of Inherent Viscosity and Ultimate Modulus Values

| Example | Inherent Viscosity | Ultimate Modulus |
|---|---|---|
| 3 | 0.572 | 2200 |
| 4 | 0.505 | 4000 |

Several of the compositions prepared in Examples 1-16, inclusive, were subjected to molecular weight determinations by means of gel permeation chromatography. The apparatus consisted of a Beckman Model 112 Solvent Delivery System (Beckman Instruments, Inc., Fullerton, Ca.), a Beckman Model 421 System Controller, and Waters 500, $10^3$, and $10^4$ Angstrom μStyragel columns (Waters Chromatography Division, Millipore Corporation, Milford, Mass.) in chloroform, HPLC-grade (Burdick and Jackson Laboratories, Inc., a subsidiary of American Hospital Supply Corporation, McGaw Park, Ill.), equilibrated at 30 degrees.

Sample injection consisted of 50 μl of a 0.5 percent, weight per volume, solution of the polymer in HPLC-grade chloroform. The flow rate of eluant (chloroform) was maintained at 1 ml per minute. Sample peaks were detected by means of changes in the refractive index using a Waters Model 410 Differential Refractometer. The calibration curves were constructed through the use of narrow molecular weight range standards covering the range from 600 to 600,000; below about 18,000, the standards were polyethylene glycols from American Polymer Standards Corporation, Mentor, Ohio, and above about b 18,000, the standards were poly(ethylene oxide) standards from Polymer Laboratories, Inc., Stow, Ohio.

Data acquisition was performed with a Nelson Analytical Model 760 Interface and an IBM Personal Computer AT (IBM Corporation, Endicott, New York), in conjuction with Nelson Analytical GPC Software, Version 3.6 (Nelson Analytical, Cupertino, Calif.), In general, the manufacturers instructions were followed. However, the most relevant data acquisition parameters were as follows:

| Minimum peak width | 15.00 seconds |
| Time for one sample | 1.50 seconds |
| Real time plot full scale for CH.O. | 500 millivolts |
| Full scale range for A.D.C. | 1 volt |
| Area reject for reference peaks | 1000.00 |

The results of the molecular weight determinations are summarized in Table 9.

TABLE 9
Summary of Results of Molecular Weight Determinations[a]

| Ex. | Peak | Area % | Peak MW | Mw[b] | Mn[c] | Mw/Mn |
|---|---|---|---|---|---|---|
| 2 | MP[d] | — | 25,425 | 190,878 | 46,656 | 4.091 |
|  | S[e] | — | 9,628 | 7,702 | 6,757 | 1.140 |
| 3' | MP | 59.7 | 28,595 | 117,424 | 41,217 | 2.849 |
|  | S | — | 16,000[f] | — | — | — |
| 5H | MP | 91.7 | 34,570 | 108,455 | 33,331 | 3.254 |
|  | S | — | 16,000[f] | — | — | — |
| 7A | MP | 80.8 | 37,764 | 307,465 | 44,458 | 6.916 |
|  | S | 9.3 | 10,621 | 9,206 | 8,534 | 1.079 |
| 8 | MP | 97.5 | 32,806 | 91,605 | 31,632 | 2.896 |
|  | S | — | 16,000[f] | — | — | — |
| 9 | MP | 92.4 | 34,570 | 139,135 | 38,201 | 3.642 |
|  | S | — | 10,000[f] | — | — | — |
| 13 | MP | 88.7 | 29,585 | 70,867 | 32,828 | 2.159 |
|  | S | 10.9 | 10,039 | 9,281 | 8,957 | 1.036 |

[a]In each case, a main peak with a shoulder was obtained.
[b]Weight average molecular weight.
[c]Number average molecular weight.
[d]Main peak.
[e]Shoulder.
[f]Approximate value.

Since the standards used to construct the calibration curves may not be the most appropriate standards for the type of polymer studied, it can be stated only that the shoulder represents a relatively low molecular weight oligomer with a narrow polydispersity. The shoulder may represent either soft segment or hard segment which was not incorporated into the polymer. On the other hand, the main peak apparently represents a relatively high molecular weight polymer with moderate to broad polydispersity. Because of the limited amount of data, correlation of polymer properties, such as water solubility and absorbency, with molecular weight and/or polydispersity is not possible.

EXAMPLES 17-22

To determine the suitability of the compositions of the present invention for the formation of nonwoven webs, several of the compositions from the above examples were extruded by means of a bench-scale apparatus having a single orifice in the die tip. The apparatus consisted of a cylindrical steel reservoir having a capacity of about 15 g. The reservoir was enclosed by an electrically heated steel jacket. The temperature of the reservoir was thermostatically controlled by means of a feedback thermocouple mounted in the body of the reservoir. The extrusion orifice had a diameter of 0.016 inch (0.41 mm) and a length of 0.060 inch (1.5 mm). A second thermocouple was mounted near the die tip. The exterior surface of the die tip was flush with the reservoir body. Polymer extrusion was accomplished by means of a compressed air piston in the reservoir. The extruded filament was surrounded and attenuated by a cylindrical air stream exiting a circular 0.075-inch (1.9-mm) gap. The forming distance was from 8 to 20 inches (20 to 51 cm). The attenuated extruded filament was collected on the clear plastic film of an 8.5×11 inch loose leaf protector having a black paper insert.

Examples 17-22, inclusive, consisted of six separate meltblowing experiments using the above-described bench-scale apparatus. Meltblowing conditions are summarized in Table 10. The table identifies the polymer employed (by reference to a previous Example), the temperatures of the reservoir, die tip, and air stream, the air pressure (in psig), and the forming distance in inches (cm).

TABLE 10
Summary of Meltblowing Conditions Using Bench-Scale Apparatus

| Example | Polymer Example | Res. Temp. | Die Temp. | Air Temp. | Air Press. | Forming Distance |
|---|---|---|---|---|---|---|
| 17 | 5A | 185 | 169 | 222 | 2 | 10 (25.4) |
| 18 | 5B | 183 | 173 | 221 | 1-2 | 10 (25.4) |
| 19 | SD & F | 180 | 179 | 216 | 1-2 | 10 (25.4) |
| 20 | 7A | 164 | 157 | 192 | 1 | 10 (25.4) |
| 21 | 11 | 227 | 209 | 264 | 10-15 | 10 (25.4) |
| 22 | 12 | 191 | 196 | 157 | 7-8 | 17-18 (43.2-45.7) |

In each case, a coherent superabsorbent nonwoven web was obtained.

EXAMPLES 23 AND 24

In a variation of the procedures described in Examples 17-22, inclusive, two of the bench scale apparatus were oriented 90 degrees from each other. One apparatus was oriented vertically with the die tip in the downward direction and the other apparatus was oriented horizontally with the die tip facing the vertically oriented apparatus. The straight-line distance between the two die tips was 5.75 inches (14.5 cm). Thus, the extruded filaments met at a point 4 inches (10.2 cm) from each die tip. The confluent filament stream was directed at a 45 degree angle from the vertical. The forming distance was either 4 or 12 inches (10.2 or 30.5 cm), measured from the point of confluence to the collecting arrangement. The collecting arrangement was a 400-openings/in$^2$ screen attached to a vacuum hose.

The vertical apparatus was charged with PF-011 polypropylene (Himont U.S.A., Inc. Wilmington, Del.). The horizontal apparatus was charged with the composition of Example 5 (specifically, a mixture of 5D and 5F).

Two experiments were conducted. In Example 23, the forming distance was 4 inches (10.2 cm) and the weight ratio of polypropylene to superabsorbent composition was approximately 60:40. In Example 24, the forming distance was 12 inches (30.5 cm) and the weight ratio of polypropylene to superabsorbent composition was approximately 70:30. The meltblowing conditions for these two Examples are summarized in Tables 11 and 12, respectively.

TABLE 11

Summary of Meltblowing Conditions for Example 23

| | Res. Temp. | Die Temp. | Air Temp. | Air Press. |
|---|---|---|---|---|
| Vertical apparatus[a] | 173 | 178 | 226 | 20 |
| Horizontal apparatus | 156 | 153 | 157,223[b] | 4,12[c] |

[a]The extrusion orifice diameter was 0.010 inch (0.25 mm).
[b]The air temperature initially was 157 degrees, but was changed to 223 degrees about halfway through the experiment.
[c]The air pressure initially was 4 psig, but was changed to psig about one-fifth of the way through the experiment.

TABLE 12

Summary of Meltblowing Conditions for Example 24

| | Res. Temp. | Die Temp. | Air Temp. | Air Press. |
|---|---|---|---|---|
| Vertical apparatus[a] | 173 | 177 | 226 | 20 |
| Horizontal apparatus | 156 | 158 | 207 | 12 |

[a]The extrusion orifice diameter was 0.010 inch (0.25 mm).

In each case, a coherent superabsorbent nonwoven web was obtained.

EXAMPLES 25–41

Since the above bench-scale meltblowing trials were successful, many of the compositions from the examples were meltblown on a pilot-scale meltblowing apparatus. Meltblowing of various of the thermoplastic superabsorbent polymers of Examples 1–16 was accomplished by extruding polymer through a 0.75-inch (19-mm) diameter Brabender extruder and through a meltblowing die having nine extrusion capillaries per linear inch (approximately 3.5 capillaries per linear cm) of die tip. Each capillary had a diameter of about 0.0145 inch (about 0.37 mm) and a length of about 0.113 inch (about 2.9 mm). The process variables in general were as follows: calculated polymer viscosity in the capillaries (in poise), polymer extrusion rate (g per capillary per min) and temperature, extrusion pressure (psig), die tip configuration which was either negative (recessed) or positive (protruding), perpendicular die tip distance, air passageway width, attenuating air temperature and pressure (psig), and forming distance. These meltblowing process variables are summarized for Examples 25–41 in Tables 13–15, inclusive.

TABLE 13

Summary of Polymer Characteristics Using Brabender Extruder

| Example | Polymer Example | Polymer Viscosity[a] |
|---|---|---|
| 25 | 5D & 5F | 1960 |
| 26 | 5D & 5F | 2110 |
| 27 | 7A | 1110 |
| 28 | 5J | 698 |
| 29 | 5J | 620 |
| 30 | 5J | 605 |
| 31 | 5J | 904 |
| 32 | 16A | 241 |
| 33 | 16B | 301 |
| 34 | 5K | 243 |
| 35 | 5H & 7B[b] | 429 |
| 36 | 16C | 738 |
| 37 | 16D | 525 |
| 38 | 16E | 219 |
| 39 | 16F | 214 |
| 40 | 16G | 939 |
| 41 | 16H | 320 |

[a]In poise at the extrusion temperature.
[b]A mixture consisting of 25 percent by weight of 5H and 75 percent by weight of 11B.

TABLE 14

Summary of Extrusion Variables Using Brabender Extruder

| | Polymer Extrusion | | | Die Tip | |
|---|---|---|---|---|---|
| Example | Rate | Temp. | Press. | Config. | Dist.[a] |
| 25 | 0.16 | 186 | 430 | — | 0.110[b] |
| 26 | 0.14 | 187 | 406 | — | 0.110 |
| 27 | 0.14 | 178 | 214 | — | 0.110 |
| 28 | 0.47 | 189 | 450 | — | 0.110 |
| 29 | 0.47 | 188 | 400 | — | 0.110 |
| 30 | 0.47 | 188 | 390 | — | 0.110 |
| 31 | 0.22 | 188 | 273 | — | 0.110 |
| 32 | 0.45 | 190 | 149 | — | 0.110 |
| 33 | 0.29 | 190 | 120 | — | 0.110 |
| 34 | 0.49 | 190 | 165 | — | 0.110 |
| 35 | 0.49 | 190 | 290 | — | 0.110 |
| 36 | 0.27 | 190 | 275 | + | 0.010[c] |
| 37 | 0.50 | 190 | 360 | + | 0.010 |
| 38 | 0.35 | 193 | 104 | + | 0.010 |
| 39 | 0.51 | 193 | 149 | + | 0.010 |
| 40 | 0.27 | 193 | 350 | + | 0.010 |
| 41 | 0.36 | 193 | 160 | — | 0.110 |

[a]Perpendicular distance in inches from the plane of the air plate lips, or perpendicular die tip distance.
[b]Or 2.8 mm.
[c]Or 0.25 mm.

TABLE 15

Summary of Attenuation Variables Using Brabender Extruder

| | | Attenuating Air | | |
|---|---|---|---|---|
| Example | APW[a] | Temp. | Press. | Forming Distance[b] |
| 25 | 0.090[c] | 412 | 1 | 38[d] |
| 26 | 0.090 | 412 | 5 | 38 |
| 27 | 0.090 | 427 | 2 | 25[e] |
| 28 | 0.090 | 432 | 1 | 25 |
| 29 | 0.090 | 432 | 2 | 25 |
| 30 | 0.090 | 420 | 4 | 25 |
| 31 | 0.090 | 430 | 0.5 | 25 |
| 32 | 0.090 | 437 | 0.75 | 25 |
| 33 | 0.090 | 435 | 1.5 | 25 |
| 34 | 0.090 | 442 | 1.5 | 25 |
| 35 | 0.090 | 433 | 1.5 | 25 |
| 36 | 0.060[f] | 430 | 0.75 | 25 |
| 37 | 0.060 | 427 | 1 | 25 |
| 38 | 0.060 | 428 | 1.5 | 25 |
| 39 | 0.060 | 418 | 1.25 | 25 |
| 40 | 0.060 | 419 | 1.25 | 25 |
| 41 | 0.090 | 419 | 2.25 | 25 |

[a]Air passageway width, in inches.
[b]In inches.
[c]Or 2.3 mm.
[d]Or 96.5 cm.
[e]Or 63.5 cm.
[f]Or 1.5 mm.

The collecting arrangement consisted of a rotating six-inch (15.2-cm) wide drum having a diameter of 30 inches (76.2 cm). The surface of the drum was a screen which had been coated with spunbound polypropylene to prevent sticking of the meltblown web to the screen. The nonwoven webs were allowed to stay on the forming screen for at least ten seconds to assure sufficient web integrity for removal and subsequent handling. Well formed, coherent, superabsorbent nonwoven webs were obtained.

The synthetic urine absorbencies of the meltblown webs obtained in Examples 28–39, inlusive, and Example 41 were determined by means of a saturated capacity test. The apparatus consisted of a stainless steel vacuum tank which was 28 cm high, 60 cm long, and 35 cm wide. The top of the tank was a removable stainless steel grid. The grid was approximately 59.5 × 34 cm and contained approximately 84 4-mm diameter holes per 100 cm². A latex rubber dam was attached to the top edge of one of the longer sides of the tank and was of a size to easily cover the grid without stretching. Evacuation of the tank was accomplished by a combination pressure/vacuum pump (Gast Manufacturing, Fisher Catalog No. 01-094, Fisher Scientific, Pittsburgh, Pa.). The pump was gaged to provide a reading of the achieved pressure reduction in inches of water which was converted to pounds per square inch (psi).

To carry out the test, at least three 3-inch (7.6-cm) square samples were cut from each meltblown web; the spunbonded carrier was removed from each sample. Each sample then was dried for at least one hour at ambient temperature under reduced pressure. For each sample, two 4-inch (10.2-cm) squares were cut from a polypropylene meltblown web having a nominal basis weight of 25-34 g/m². Each sample and the accompanying two squares of polypropylene meltblown web were weighed separately.

The sample was placed on one polypropylene square and immersed, with the sample underneath the polypropylene square, for 30 minutes in a bath of synthetic urine at 37 degrees (98.6 degrees F). The sample was removed carefully from the bath and placed on the second polypropylene square which was on the vacuum tank grid, the sample being sandwiched between the two polypropylene squares. After draining for one minute, the sample sandwich was weighed.

The sample sandwich was placed on the grid. The grid was covered completely with the rubber dam and the pressure in the tank was reduced to 0.5 psi less than atmospheric pressure; i.e., the pressure differential from one side of the sample sandwich to the other was 0.5 psi. This pressure differential was maintained for 5 minutes, after which time the sample sandwich was weighed. This procedure was repeated three additional times at pressure differentials of 1.0, 2.0, and 3.0 psi. After the sample sandwich weighing at the 3.0-psi differential, the sample was removed from the sandwich and weighed separately.

In order to calculate an absorbence at each pressure differential, it was necessary to correct each sandwich weight for the weight of the wet polypropylene squares (WPPS). This was done by subtracting the sample weight at the 3.0-psi pressure differential from the sandwich weight at the same pressure differential. The absorbence (A) for each sample at each pressure differential then was calculated as follows:

$A = (\text{wt. sandwich} - \text{wt. WPPS} - \text{wt. dry sample})/\text{wt. dry sample}$ Thus, the absorbence value at each pressure differential is the number of g of synthetic urine absorbed per g of sample.

The results of the saturated capacity test are summarized in Table 16. The absorbencies reported are averages of at least three samples.

TABLE 16

Summary of Saturated Capacity Test on Meltblown Webs from Examples 28-39, 41

| Example | Absorbency, g Syn. Urine/g | | | |
|---|---|---|---|---|
| | 0.5 psi | 1.0 psi | 2.0 psi | 3.0 psi |
| 28 | 19.91 | 17.09 | 15.52 | 14.17 |
| 29 | 23.00 | 19.36 | 18.06 | 16.46 |
| 30 | 25.65 | 21.42 | 19.02 | 16.86 |
| 31 | 25.43 | 22.36 | 19.61 | 17.76 |
| 32 | 9.56 | 9.40 | 9.14 | 8.92 |
| 33 | 11.16 | 10.91 | 10.64 | 10.37 |

TABLE 16-continued

Summary of Saturated Capacity Test on Meltblown Webs from Examples 28-39, 41

| Example | Absorbency, g Syn. Urine/g | | | |
|---|---|---|---|---|
| | 0.5 psi | 1.0 psi | 2.0 psi | 3.0 psi |
| 34 | 11.16 | 10.94 | 10.54 | 10.13 |
| 35 | 7.68 | 7.60 | 7.45 | 7.33 |
| 36 | 15.77 | 13.82 | 12.69 | 11.91 |
| 37 | 17.92 | 16.82 | 16.33 | 15.75 |
| 38 | 12.39 | 11.90 | 11.59 | 11.30 |
| 39 | 15.70 | 14.62 | 13.82 | 13.20 |
| 41 | 17.69 | 16.16 | 14.45 | 13.26 |

It should be noted that the data in Tables 7 and 16, respectively, were obtained by two different test procedures. Moreover, the data in Table 7 were obtained with polymer films, whereas the data in Table 16 were obtained with meltblown webs.

Larger scale meltblowing runs were carried out, primarily to prepare coformed webs essentially as described hereinbefore and illustrated by FIG. 5. These larger scale runs are described in Examples 42-66, inclusive, below. In each case the superabsorbent thermoplastic composition employed was that of Example 16.

EXAMPLE 42

A fibrous coformed nonwoven web was formed by meltblowing a superabsorbent thermoplastic composition of the present invention and incorporating polyester staple fibers therein.

Meltblowing of the superabsorbent thermoplastic composition was accomplished by extruding the composition from a 1.5-inch (3.75-cm) Johnson extruder and through a meltblowing die having 15 extrusion capillaries per linear inch (about 5.9 extrusion capillaries per linear cm) of die tip. Each capillary had a diameter of about 0.018 inch (about 0.46 mm) and a length of about 0.14 inch (about 3.6 mm). The composition was extruded through the capillaries at a rate of about 0.50 g per capillary per minute at a temperature of about 184 degrees. The extrusion pressure exerted on the composition in the die tip was in the range of from about 180 to 200 psig. The composition viscosity in the die tip under these conditions was about 500 poise. The die tip configuration was adjusted to have a positive perpendicular die tip distance of about 0.010 inch (about 0.25 mm). The air gaps of the two attenuating air passageways were adjusted to be about 0.060 inch (about 0.15 mm). Forming air for meltblowing the composition was supplied to the air passageways at a temperature of about 209 degrees and a pressure of about 2 psig. The fibers thus formed were deposited on a forming screen drum which was approximately 18 inches (46 cm) below and 20 inches (51 cm) back from the die tip.

Following the procedure illustrated by FIG. 5 and described earlier, 1.5-inch (3.75-cm) long, 15 denier per filament polyester staple was incorporated into the stream of meltblown fibers prior to deposition upon the forming drum. The polyester fibers were first formed by a Rando Webber mat-forming apparatus into a mat having a basis weight of about 100 g/m². The mat was fed to the picker roll by a feed roll which was positioned about 0.007 inch (about 0.18 mm) from the picker roll surface. The picker roll was rotating at a rate of about 3,000 revolutions per minute and fiber transporting air was supplied to the picker roll at a pressure of about 3 psig. While actual measurement of the position of the nozzle of the coform apparatus with respect to the stream of meltblown fiber was not made, it was estimated to be about 2 inches (about 5.1 cm) below and about 2 inches (5.1 cm) away from the die tip of the meltblowing die.

A coformed nonwoven web was formed which had a width (cross-machine direction) of about 20 inches (about 51 cm) and which was composed of about 25 percent by weight of the meltblown fibers and about 75 percent by weight of the polyester fibers. The web had a basis weight of about 200 g/m².

EXAMPLE 43

The procedure of Example 42 was repeated, except that the coformed web was composed of about 50 percent by weight of the meltblown fibers and about 50 percent by weight of the polyester fibers.

EXAMPLE 44

The procedure of Example 43 was repeated, except that the basis weight of the coformed web was about 400 g/m2

EXAMPLE 44

The procedure of Example 42 was repeated, except that the coformed web was composed of about 75 percent by weight of the meltblown fibers and about 25 percent by weight of the polyester fibers.

EXAMPLE 46

The procedure of Example 45 was repeated, except that the staple was 2-inch (5.1-cm) long, 5.5 denier per filament polyester staple.

EXAMPLE 47

The procedure of Example 46 was repeated, except that the coformed web was composed of about 50 percent by weight of the meltblown fibers and about 50 percent by weight of the polyester fibers.

The procedure of Example 46 was repeated, except that the coformed web was composed of about 25 percent by weight of the meltblown fibers and about 75 percent by weight of the polyester fibers.

EXAMPLE 49

A fibrous coformed nonwoven web was formed by meltblowing a superabsorbent thermoplastic composition of the present invention and incorporating pulp fibers therein.

Meltblowing of the superabsorbent thermoplastic composition was accomplished by extruding the composition from a 1.5-inch (3.75-cm) Johnson extruder and through a meltblowing die having 15 extrusion capillaries per linear inch (about 5.9 extrusion capillaries per linear cm) of die tip. Each capillary had a diameter of about 0.018 inch (about 0.46 mm) and a length of about 0.14 inch (about 3.6 mm). The composition was extruded through the capillaries at a rate of about 0.50 g per capillary per minute at a temperature of about 184 degrees. The extrusion pressure exerted on the composition in the die tip was in the range of from about 180 to 200 psig. The composition viscosity in the die tip under these conditions was about 500 poise. The die tip configuration was adjusted to have a positive perpendicular die tip distance of about 0.010 inch (about 0.25 mm). The air gaps of the two attenuating air passageways were adjusted to be about 0.060 inch (about 0.15 mm). Forming air for meltblowing the composition was supplied to the air passageways at a temperature of about 209 degrees and a pressure of about 2 psig. The fibers thus formed were deposited on a forming screen drum which was approximately 18 inches (46 cm) below and 20 inches (51 cm) back from the die tip.

Following the procedure illustrated by FIG. 5 and described earlier, International Paper Super Soft pulp fibers were incorporated into the stream of meltblown fibers prior to deposition upon the forming drum. The pulp fibers were first formed by a Rando Webber mat-forming apparatus into a mat having a basis weight of about 200 gm². The mat was fed to the picker roll by a feed roll which was positioned about 0.030 inch (about 0.76 mm) from the picker roll surface. The picker roll was rotating at a rate of about 3,000 revolutions per minute and fiber transporting air was supplied to the picker roll at a pressure of about 3 psig. While actual measurement of the position of the nozzle of the coform apparatus with respect to the stream of meltblown fiber was not made, it was estimated to be about 2 inches (about 5.1 cm) below and about 2 inches (5.1 cm) away from the die tip of the meltblowing die.

A coformed nonwoven web was formed which had a width (cross-machine direction) of about 20 inches (about 51 cm) and which was composed of about 50 percent by weight of the meltblown fibers and about 50 percent by weight of the pulp fibers. The web had a basis weight of about 200 g/m².

EXAMPLE 50

The procedure of Example 49 was repeated, except that the coformed web was composed of about 25 percent by weight of the meltblown fibers and about 75 percent by weight of the pulp fibers and had a basis weight of about 400 g/m².

EXAMPLE 51

The procedure of Example 50 was repeated, except that the coformed web was composed of about 50 percent by weight of the meltblown fibers and about 50 percent by weight of the pulp fibers.

EXAMPLE 52

The procedure of Example 51 was repeated, except that the basis weight of the coformed web was about 200 g/m².

EXAMPLE 53

A fibrous nonwoven web was formed by meltblowing a superabsorbent thermoplastic composition of the present invention.

Meltblowing of the superabsorbent thermoplastic composition was accomplished by extruding the composition from a 1.5-inch (3.75-cm) Johnson extruder and through a meltblowing die having 15 extrusion capillaries per linear inch (about 5.9 extrusion capillaries per linear cm) of die tip. Each capillary had a diameter of about 0.018 inch (about 0.46 mm) and a length of about 0.14 inch (about 3.6 mm). The composition was extruded through the capillaries at a rate of about 0.25 g per capillary per minute at a temperature of about 181 degrees. The extrusion pressure exerted on the composition in the die tip was 282 psig. The composition viscosity in the die tip under these conditions was about 1500 poise. The die tip configuration was adjusted to have a positive perpendicular die tip distance of about 0.010 inch (about 0.25 mm). The air gaps of the two attenuating air passageways were adjusted to be about 0.060 inch (about 0.15 mm). Forming air for meltblowing the composition was supplied to the air passageways at a temperature of about 197 degrees and a pressure of about 3 psig. The fibers thus formed were deposited on a forming screen drum which was approximately 7.5 inches (19 cm) from the die tip.

A nonwoven web was formed which had a width (cross-machine direction) of about 20 inches (about 51 cm) and a basis weight of about 60 g/m².

EXAMPLE 54

The procedure of Example 53 was repeated, except that the forming air for meltblowing was supplied at a pressure of about 6 psig and the forming screen drum was about 17 inches (about 43.2 cm) from the die tip.

EXAMPLE 55

A fibrous coformed nonwoven web was formed by meltblowing a superabsorbent thermoplastic composition of the present invention and incorporating polyester staple fibers therein.

Meltblowing of the superabsorbent thermoplastic composition was accomplished by extruding the composition from a 1.5-inch (3.75-cm) Johnson extruder and through a meltblowing die having 15 extrusion capillaries per linear inch (about 5.9 extrusion capillaries per linear cm) of die tip. Each capillary had a diameter of about 0.018 inch (about 0.46 mm) and a length of about 0.14 inch (about 3.6 mm). The composition was extruded through the capillaries at a rate of about 0.25 g per capillary per minute at a temperature of about 181 degrees. The extrusion pressure exerted on the composition in the die tip was 282 psig. The composition viscosity in the die tip under these conditions was about 1500 poise. The die tip configuration was adjusted to have a positive perpendicular die tip distance of about 0.010 inch (about 0.25 mm). The air gaps of the two attenuating air passageways were adjusted to be about 0.060 inch (about 0.15 mm). Forming air for meltblowing the composition was supplied to the air passageways at a temperature of about 197 degrees and a pressure of about 3 psig. The fibers thus formed were deposited on a forming screen drum which was approximately 7.5 inches (19 cm) from the die tip.

Following the procedure illustrated by FIG. 5 and described earlier, 1.5-inch (3.75-cm) long, 15 denier per filament polyester staple was incorporated into the stream of meltblown fibers prior to deposition upon the forming drum. The polyester fibers were first formed by a Rando Webber mat-forming apparatus into a mat having a basis weight of about 100 g/m². The mat was fed to the picker roll by a feed roll which was positioned about 0.005 inch (about 0.13 mm) from the picker roll surface. The picker roll was rotating at a rate of about 3,000 revolutions per minute and fiber transporting air was supplied to the picker roll at a pressure of about 3 psig. While actual measurement of the position of the nozzle of the coform apparatus with respect to the stream of meltblown fiber was not made, it was estimated to be about 2 inches (about 5.1 cm) below and about 2 inches (5.1 cm) away from the die tip of the meltblowing die.

A coformed nonwoven web was formed which had a width (cross-machine direction) of about 20 inches (about 51 cm) and which was composed of about 30 percent by weight of the meltblown fibers and about 70 percent by weight of the polyester fibers. The web had a basis weight of about 200 g/m².

EXAMPLE 56

The procedure of Example 55 was repeated, except that the forming air for meltblowing was supplied at a pressure of about 6 psig, the forming screen drum was about 17 inches (about 43.2 cm) from the die tip, and the fiber transporting air was supplied to the picker roll at a pressure of about 2 psig.

EXAMPLE 57

The procedure of Example 56 was repeated, except that the coformed web was composed of about 60 percent by weight of meltblown fibers and about 40 percent by weight of the polyester fibers and the basis weight of the web was about 160 g/m².

EXAMPLE 58

A fibrous coformed nonwoven web was formed by meltblowing a superabsorbent thermoplastic composition of the present invention and incorporating polyester staple fibers therein.

Meltblowing of the superabsorbent thermoplastic composition was accomplished by extruding the composition from a 1.5-inch (3.75-cm) Johnson extruder and through a meltblowing die having 15 extrusion capillaries per linear inch (about 5.9 extrusion capillaries per linear cm) of die tip. Each capillary had a diameter of about 0.018 inch (about 0.46 mm) and a length of about 0.14 inch (about 3.6 mm). The composition was extruded through the capillaries at a rate of about 0.40 g per capillary per minute at a temperature of about 204 degrees. The extrusion pressure exerted on the composition in the die tip was about 288 psig. The composition viscosity in the die tip under these conditions was about 950 poise. The die tip configuration was adjusted to have a positive perpendicular die tip distance of about 0.010 inch (about 0.25 mm). The air gaps of the two attenuating air passageways were adjusted to be about 0.060 inch (about 0.15 mm). Forming air for meltblowing the composition was supplied to the air passageways at a temperature of about 231 degrees and a pressure of about 3 psig. The fibers thus formed were deposited on a forming screen drum which was approximately 17 inches (43.2 cm) from the die tip.

Following the procedure illustrated by FIG. 5 and described earlier, 1.5-inch (3.75-cm) long, 15 denier per filament polyester staple was incorporated into the stream of meltblown fibers prior to deposition upon the forming drum. The polyester fibers were first formed by a Rando Webber mat-forming apparatus into a mat having a basis weight of about 100 g/m². The mat was fed to the picker roll by a feed roll which was positioned about 0.005 inch (about 0.13 mm) from the picker roll surface. The picker roll was rotating at a rate of about 3,000 revolutions per minute and fiber transporting air was supplied to the picker roll at a pressure of about 2 psig. While actual measurement of the position of the nozzle of the coform apparatus with respect to the stream of meltblown fiber was not made, it was estimated to be about 2 inches (about 5.1 cm) below and about 2 inches (5.1 cm) away from the die tip of the meltblowing die.

A coformed nonwoven web was formed which had a width (cross-machine direction) of about 20 inches (about 51 cm) and which was composed of about 60 percent by weight of the meltblown fibers and about 40 percent by weight of the polyester fibers. The web had a basis weight of about 200 g/m².

EXAMPLE 59

A fibrous coformed nonwoven web was formed by meltblowing a superabsorbent thermoplastic composition of the present invention and incorporating pulp fibers therein.

Meltblowing of the superabsorbent thermoplastic composition was accomplished by extruding the composition from a 1.5-inch (3.75-cm) Johnson extruder and through a meltblowing die having 15 extrusion capillaries per linear inch (about 5.9 extrusion capillaries per linear cm) of die tip. Each capillary had a diameter of about 0.018 inch (about 0.46 mm) and a length of about 0.14 inch (about 3.6 mm). The composition was extruded through the capillaries at a rate of about 0.35 g per capillary per minute at a temperature of about 194 degrees. The extrusion pressure exerted on the composition in the die tip was about 273 psig. The composition viscosity in the die tip under these conditions was about 1030 poise. The die tip configuration was adjusted to have a positive perpendicular die tip distance of about 0.010 inch (about 0.25 mm). The air gaps of the two attenuating air passageways were adjusted to be about 0.060 inch (about 0.15 mm). Forming air for meltblowing the composition was supplied to the air passageways at a temperature of about 206 degrees and a pressure of about 3 psig. The fibers thus formed were eposited on a forming screen drum which was approximately 7.5 inches (19 cm) from the die tip.

Following the procedure illustrated by FIG. 5 and described earlier, International Paper Super Soft pulp fibers were incorporated into the stream of meltblown fibers prior to deposition upon the forming drum. The pulp fibers were first formed by a Rando Webber mat-forming apparatus into a mat having a basis weight of about 200 g/m$^2$. The mat was fed to the picker roll by a feed roll which was estimated to be about 0.030 inch (about 0.76 mm) from the picker roll surface. The picker roll was rotating at a rate of about 3,000 revolutions per minute and fiber transporting air was supplied to the picker roll at a pressure of about 3 psig. While actual measurement of the position of the nozzle of the coform apparatus with respect to the stream of meltblown fiber was not made, it was estimated to be about 2 inches (about 5.1 cm) below and about 2 inches (5.1 cm) away from the die tip of the meltblowing die.

A coformed nonwoven web was formed which had a width (cross-machine direction) of about 20 inches (about 51 cm) and which was composed of about 30 percent by weight of the meltblown fibers and about 70 percent by weight of the pulp fibers. The web had a basis weight of about 200 g/m$^2$.

EXAMPLE 60

The procedure of Example 59 was repeated, except that the forming air for meltblowing was supplied at a pressure of about 6 psig and the forming screen drum was about 17 inches (about 43.2 cm) from the die tip.

EXAMPLE 61

A fibrous coformed nonwoven web was formed by meltblowing a superabsorbent thermoplastic composition of the present invention and incorporating pulp fibers therein.

Meltblowing of the superabsorbent thermoplastic composition was accomplished by extruding the composition from a 1.5-inch (3.75-cm) Johnson extruder and through a meltblowing die having 15 extrusion capillaries per linear inch (about 5.9 exrrusion capillaries per linear cm) of die tip. Each capillary had a diameter of about 0.018 inch (about 0.46 mm) and a length of about 0.14 inch (about 3.6 mm). The composition was extruded through the capillaries at a rate of about 0.35 g per capillary per minute at a temperature of about 196 degrees. The extrusion pressure exerted on the composition in the die tip was about 253 psig. The composition viscosity in the die tip under these conditions was about 960 poise. The die tip configuration was adjusted to have a positive perpendicular die tip distance of about 0.010 inch (about 0.25 mm). The air gaps of the two attenuating air passageways were adjusted to be about 0.060 inch (about 0.15 mm). Forming air for meltblowing the composition was supplied to the air passageways at a temperature of about 206 degrees and a pressure of about 6 psig. The fibers thus formed were deposited on a forming screen drum which was approximately 7.5 inches (19 cm) below and 20 inches (51 cm) from the die tip.

Following the procedure illustrated by FIG. 5 and described earlier, International Paper Super Soft pulp fibers were incorporated into the stream of meltblown fibers prior to deposition upon the forming drum. The pulp fibers were first formed by a Rando Webber mat-forming apparatus into a mat having a basis weight of about 200 g/m$^2$. The mat was fed to the picker roll by a feed roll which was estimated to be about 0.030 inch (about 0.76 mm) from the picker roll surface. The picker roll was rotating at a rate of about 3,000 revolutions per minute and fiber transporting air was supplied to the picker roll at a pressure of about 3 psig. While actual measurement of the position of the nozzle of the coform apparatus with respect to the stream of meltblown fiber was not made, it was estimated to be about 2 inches (about 5.1 cm) below and about 2 inches (5.1 cm) away from the die tip of the meltblowing die.

A coformed nonwoven web was formed which had a width (cross-machine direction) of about 20 inches (about 51 cm) and which was composed of about 30 percent by weight of the meltblown fibers and about 70 percent by weight of the pulp fibers. The web had a basis weight of about 200 g/m$^2$.

EXAMPLE 62

A fibrous coformed nonwoven web was formed by meltblowing a superabsorbent thermoplastic composition of the present invention and incorporating pulp fibers therein.

Meltblowing of the superabsorbent thermoplastic composition was accomplished by extruding the composition from a 1.5-inch (3.75-cm) Johnson extruder and through a meltblowing die having 15 extrusion capillaries per linear inch (about 5.9 extrusion capillaries per linear cm) of die tip. Each capillary had a diameter of about 0.018 inch (about 0.46 mm) and a length of about 0.14 inch (about 3.6 mm). The composition was extruded through the capillaries at a rate of about 0.35 g per capillary per minute at a temperature of about 195 degrees. The extrusion pressure exerted on the composition in the die tip was about 259 psig. The composition viscosity in the die tip under these conditions was about 980 poise. The die tip configuration was adjusted to have a positive perpendicular die tip distance of about 0.010 inch (about 0.25 mm). The air gaps of the two attenuating air passageways were adjusted to be about 0.060 inch (about 0.15 mm). Forming air for meltblowing the composition was supplied to the air passageways at a temperature of about 206 degrees and a pressure of about 3 psig. The fibers thus formed were deposited on a forming screen drum which was approximately 7.5 inches (19 cm) from the die tip.

Following the procedure illustrated by FIG. 5 and described earlier, International Paper Super Soft pulp fibers were incorporated into the stream of meltblown fibers prior to deposition upon the forming drum. The pulp fibers were first formed by a Rando Webber mat-forming apparatus into a mat having a basis weight of about 200 g/m$^2$. The mat was fed to the picker roll by a feed roll which was estimated to be about 0.030 inch (about 0.76 mm) from the picker roll surface. The picker roll was rotating at a rate of about 3,000 revolutions per minute and fiber transporting air was supplied to the picker roll at a pressure of about 3 psig. While actual measurement of the position of the nozzle of the coform apparatus with respect to the stream of meltblown fiber was not made, it was estimated to be about 2 inches (about 5.1 cm) below and about 2 inches (5.1 cm) away from the die tip of the meltblowing die.

A coformed nonwoven web was formed which had a width (cross-machine direction) of about 20 inches (about 51 cm) and which was composed of about 30 percent by weight of the meltblown fibers and about 70 percent by weight of the pulp fibers. The web had a basis weight of about 250 g/m$^2$.

EXAMPLE 63

The procedure of Example 62 was repeated, except that the fiber transporting air was supplied to the picker roll at a pressure of about 2 psig, the coformed web was composed of about 40 percent by weight of the meltblown fibers and about 60 percent of the pulp fibers, and the web basis weight was about 216 g/m$^2$.

EXAMPLE 64

A fibrous coformed nonwoven web was formed by meltblowing a superabsorbent thermoplastic composition of the present invention and incorporating pulp fibers therein.

Meltblowing of the superabsorbent thermoplastic composition was accomplished by extruding the composition from a 1.5-inch (3.75-cm) Johnson extruder and through a meltblowing die having 15 extrusion capillaries per linear inch (about 5.9 extrusion capillaries per linear cm) of die tip. Each capillary had a diameter of about 0.018 inch (about 0.46 mm) and a length of about 0.14 inch (about 3.6 mm). The composition was extruded through the capillaries at a rate of about 0.35 g per capillary per minute at a temperature of about 196 degrees. The extrusion pressure exerted on the composition in the die tip was about 250 psig. The composition viscosity in the die tip under these conditions was about 950 poise. The die tip configuration was adjusted to have a positive perpendicular die tip distance of about 0.010 inch (about 0.25 mm). The air gaps of the two attenuating air passageways were adjusted to be about 0.060 inch (about 0.15 mm). Forming air for meltblowing the composition was supplied to the air passageways at a temperature of about 206 degrees and a pressure of about 3 psig. The fibers thus formed were deposited on a forming screen drum which was approximately 7.5 inches (19 cm) from the die tip.

Following the procedure illustrated by FIG. 5 and described earlier, Weyerhauser NB-309 pulp fibers were incorporated into the stream of meltblown fibers prior to deposition upon the forming drum. The pulp fibers were first formed by a Rando Webber mat-forming apparatus into a mat having a basis weight of about 200 g/m$^2$. The mat was fed to the picker roll by a feed roll which was estimated to be about 0.030 inch (about 0.76 mm) from the picker roll surface. The picker roll was rotating at a rate of about 3,000 revolutions per minute and fiber transporting air was supplied to the picker roll at a pressure of about 2 psig. While actual measurement of the position of the nozzle of the coform apparatus with respect to the stream of meltblown fiber was not made, it was estimated to be about 2 inches (about 5.1 cm) below and about 2 inches (5.1 cm) away from the die tip of the meltblowing die.

A coformed nonwoven web was formed which had a width (cross-machine direction) of about 20 inches (about 51 cm) and which was composed of about 44 percent by weight of the meltblown fibers and about 56 percent by weight of the pulp fibers. The web had a basis weight of about 250 g/m$^2$.

EXAMPLE 65

A fibrous coformed nonwoven web was formed by meltblowing a superabsorbent thermoplastic composition of the present invention and incorporating pulp fibers therein.

Meltblowing of the superabsorbent thermoplastic composition was accomplished by extruding the composition from a 1.5-inch (3.75-cm) Johnson extruder and through a meltblowing die having 15 extrusion capillaries per linear inch (about 5.9 extrusion capillaries per linear cm) of die tip. Each capillary had a diameter of about 0.018 inch (about 0.46 mm) and a length of about 0.14 inch (about 3.6 mm). The composition was extruded through the capillaries at a rate of about 0.35 g per capillary per minute at a temperature of about 206 degrees. The extrusion pressure exerted on the composition in the die tip was about 252 psig. The composition viscosity in the die tip under these conditions was about 955 poise. The die tip configuration was adjusted to have a positive perpendicular die tip distance of about 0.010 inch (about 0.25 mm). The air gaps of the two attenuating air passageways were adjusted to be about 0.060 inch (about 0.15 mm). Forming air for meltblowing the composition was supplied to the air passageways at a temperature of about 207 degrees and a pressure of about 6 psig. The fibers thus formed were deposited on a forming screen drum which was approximately 7.5 inches (19 cm) from the die tip.

Following the procedure illustrated by FIG. 5 and described earlier, Weyerhauser NB-309 pulp fibers were incorporated into the stream of meltblown fibers prior to deposition upon the forming drum. The pulp fibers were first formed by a Rando Webber mat-forming apparatus into a mat having a basis weight of about 200 g/m$^2$. The mat was fed to the picker roll by a feed roll which was estimated to be about 0.030 inch (about 0.76 mm) from the picker roll surface. The picker roll was rotating at a rate of about 3,000 revolutions per minute and fiber transporting air was supplied to the picker roll at a pressure of about 2 psig. While actual measurement of the position of the nozzle of the coform apparatus with respect to the stream of meltblown fiber was not made, it was estimated to be about 2 inches (about 5.1 cm) below and about 2 inches (5.1 cm) away from the die tip of the meltblowing die.

A coformed nonwoven web was formed which had a width (cross-machine direction) of about 20 inches (about 51 cm) and which was composed of about 44 percent by weight of the meltblown fibers and about 56 percent by weight of the pulp fibers. The web had a basis weight of about 250 g/m².

EXAMPLE 66

A fibrous coformed nonwoven web was formed by meltblowing a superabsorbent thermoplastic composition of the present invention and incorporating pulp fibers therein.

Meltblowing of the superabsorbent thermoplastic composition was accomplished by extruding the composition from a 1.5-inch (3.75-cm) Johnson extruder and through a meltblowing die having 15 extrusion capillaries per linear inch (about 5.9 extrusion capillaries per linear cm) of die tip. Each capillary had a diameter of about 0.018 inch (about 0.46 mm) and a length of about 0.14 inch (about 3.6 mm). The composition was extruded through the capillaries at a rate of about 0.35 g per capillary per minute at a temperature of about 196 degrees. The extrusion pressure exerted on the composition in the die tip was about 250 psig. The composition viscosity in the die tip under these conditions was about 945 poise. The die tip configuration was adjusted to have a positive perpendicular die tip distance of about 0.010 inch (about 0.25 mm). The air gaps of the two attenuating air passageways were adjusted to be about 0.060 inch (about 0.15 mm). Forming air for meltblowing the composition was supplied to the air passageways at a temperature of about 206 degrees and a pressure of about 6 psig. The fibers thus formed were deposited on a forming screen drum which was approximately 7.5 inches (19 cm) from the die tip.

Following the procedure illustrated by FIG. 5 and described earlier, Weyerhauser NB-309 pulp fibers were incorporated into the stream of meltblown fibers prior to deposition upon the forming drum. The pulp fibers were first formed by a Rando Webber mat-forming apparatus into a mat having a basis weight of about 200 g/m². The mat was fed to the picker roll by a feed roll which was estimated to be about 0.030 inch (about 0.76 mm) from the picker roll surface. The picker roll was rotating at a rate of about 3,000 revolutions per minute and fiber transporting air was supplied to the picker roll at a pressure of about 2 psig. While actual measurement of the position of the nozzle of the coform apparatus with respect to the stream of meltblown fiber was not made, it was estimated to be about 2 inches (about 5.1 cm) below and about 2 inches (5.1 cm) away from the die tip of the meltblowing die.

A coformed nonwoven web was formed which had a width (cross-machine direction) of about 20 inches (about 51 cm) and which was composed of about 30 percent by weight of the meltblown fibers and about 70 percent by weight of the pulp fibers. The web had a basis weight of about 200 g/m².

The nonwoven webs obtained in Examples 43-50 and 53-66, inclusive, were subjected to the saturated capacity test to determine synthetic urine absorbencies. The results are summarized in Table 17; the absorbency values reported are averages of at least three samples. It perhaps should be noted that the test procedure this time did not require the removal of a spunbound carrier since such carrier was not employed.

TABLE 17

Summary of Saturated Capacity Test on Nonwoven Webs from Examples 42-50 and 53-66

| Example | Absorbency, g Syn. Urine/g | | | |
|---|---|---|---|---|
| | 0.5 psi | 1.0 psi | 2.0 psi | 3.0 psi |
| 42 | 9.0 | 6.8 | 5.9 | 5.3 |
| 43 | 11.8 | 9.8 | 8.9 | 8.4 |
| 44 | 8.9 | 7.7 | 7.4 | 7.2 |
| 45 | 12.8 | 12.0 | 11.7 | 11.5 |
| 46 | 11.3 | 10.2 | 9.7 | 9.5 |
| 47 | 10.5 | 9.0 | 8.6 | 8.3 |
| 48 | 9.2 | 8.5 | 7.9 | 7.2 |
| 49 | 7.3 | 6.0 | 5.0 | 4.8 |
| 50 | 7.4 | 5.8 | 4.8 | 4.7 |
| 53 | 9.5 | 9.3 | 9.0 | 8.7 |
| 54 | 13.8 | 13.1 | 12.3 | 11.3 |
| 55 | 10.4 | 8.1 | 6.9 | 6.2 |
| 56 | 9.4 | 8.0 | 6.5 | 5.6 |
| 57 | 10.8 | 8.3 | 7.2 | 6.5 |
| 58 | 13.7 | 12.5 | 11.7 | 11.1 |
| 59 | 9.0 | 7.2 | 5.7 | 4.9 |
| 60 | 7.9 | 6.3 | 5.0 | 4.3 |
| 61 | 8.3 | 6.5 | 5.3 | 4.8 |

Having thus described the invention, numerous changes and modifications thereto will be apparent to those having ordinary skill in the art without departing from the spirit and scope of the present invention.

What is claimed is:

1. A nonwoven web comprising fibers composed of a superabsorbent, thermoplastic polymeric composition comprising:
   (A) from about 86 to about 98 percent by weight, based on the total weight of the composition, of a poly(oxyethylene) soft segment having a weight average molecular weight in the range of from about 5,000 to about 50,000; and
   (B) from about 2 to about 14 percent by weight, based on the total weight of the composition, of a hard segment which has a melting point above ambient temperature and below the temperature at which decomposition of either the composition or the soft segment takes place, is essentially insoluble in water, and phase separates from the soft segment, said hard segment being selected from the group consisting of polyurethanes, polyamides, polyesters, polyureas, and combinations thereof;

wherein the soft and hard segments are covalently bound together by means of urethane, amide, ester, or secondary urea linkages or combinations thereof.

2. The nonwoven web of claim 1, in which said fibers include polycomponent fibers, at least one component of which is said superabsorbent, thermoplastic polymeric composition.

3. The nonwoven web of claim 2, in which said polycomponent fibers are bicomponent fibers.

4. The nonwoven web of claim 3, in which said bicomponent fibers are sheath-core fibers.

5. The nonwoven web of claim 4, in which the sheath is said superabsorbent, thermoplastic polymeric composition and the core is a polyolefin.

6. The nonwoven web of claim 5, in which said polyolefin is polypropylene or polyethylene.

7. The nonwoven web of claim 1, in which the weight average molecular weight of said soft segment is in the range of from about 8,000 to about 50,000.

8. The nonwoven web of claim 7, in which the weight average molecular weight of said soft segment is in the range of from about 8,000 to about 30,000.

9. The nonwoven web of claim 8, in which the weight average molecular weight of said soft segment is in the range of from about 8,000 to about 16,000.

10. The nonwoven web of claim 1, in which said soft segment is present in the range of from about 90 to about 97 percent by weight.

11. The nonwoven web of claim 10, in which said soft segment is present in the range of from about 95 to 97 percent by weight.

12. The nonwoven web of claim 1, in which said hard segment is present in the range of from about 3 to about 10 percent by weight.

13. The nonwoven web of claim 12, in which said hard segment is present in the range of from about 3 to about 5 percent by weight.

14. The nonwoven web of claim 1, in which said soft segment is derived from a poly(oxyethylene) diol.

15. The nonwoven web of claim 14, in which said hard segment is a polyurethane.

16. The nonwoven web of claim 15, in which said polyurethane is derived from 1,4-butanediol.

17. A nonwoven web comprising a plurality of substantially identically prepared discontinuous and substantially randomly deposited monofilaments of a superabsorbent, thermoplastic polymeric composition comprising:
(A) from about 86 to about 98 percent by weight, based on the total weight of the composition, of a poly(oxyethylene) soft segment having a weight average molecular weight in the range or from about 5,000 to about 50,000; and
(B) from about 2 to about 14 percent by weight, based on the total weight of the composition, of a hard segment which has a melting point above ambient temperature and below the temperature at which decomposition of either the composition or the soft segment takes place, is essentially insoluble in water, and phase separates from the soft segment, said hard segment being selected from the group consisting of polyurethanes, polyamides, polyesters, polyureas, and combinations thereof;
wherein the soft and hard segments are covalently bound together by means of urethane, amide, ester, or secondary urea linkages or combinations thereof.

18. The nonwoven web of claim 17, in which the weight average molecular weight of said soft segment is in the range of from about 8,000 to about 50,000.

19. The nonwoven web of claim 18, in which the weight average molecular weight of said soft segment is in the range of from about 8,000 to about 30,000.

20. The nonwoven web of claim 19 in which the weight average molecular weight of said soft segment is in the range of from about 8,000 to about 16,000.

21. The nonwoven web of claim 17, in which said soft segment is present in the range of from about 90 to about 97 percent by weight.

22. The nonwoven web of claim 21, in which said soft segment is present in the range of from about 95 to about 97 percent by weight.

23. The nonwoven web of claim 17, in which said hard segment is present in the range of from about 3 to about 10 percent by weight.

24. The nonwoven web of claim 23, in which said hard segment is present in the range of from about 3 to about 5 percent by weight.

25. The nonwoven web of claim 17, in which said soft segment is derived from a poly(oxyethylene) diol.

26. The nonwoven web of claim 25, in which said hard segment is a polyurethane.

27. The nonwoven web of claim 26, in which said polyurethanes is derived from 1,4-butanediol.

28. A nonwoven web comprising a plurality of substantially identically prepared continuous and substantially randomly deposited monofilaments of a superabsorbent, thermoplastic polymeric composition comprising:
(A) from about 86 to about 98 percent by weight, based on the total weight of the composition, of a poly(oxyethylene) soft segment having a weight average molecular weight in the range of from about 5,000 to about 50,000; and
(B) from about 2 to about 14 percent by weight, based on the total weight of the composition, of a hard segment which has a melting point above ambient temperature and below the temperature at which decomposition of either the composition or the soft segment takes place, is essentially insoluble in water, and phase separates from the soft segment, said hard segment being selected from the group consisting of polyurethanes, polyamides, polyesters, polyureas, and combinations thereof;
wherein the soft and hard segments are covalently bound together by means of urethane, amide, ester, or secondary urea linkages or combinations thereof.

29. The nonwoven web of claim 28, in which the weight average molecular weight of said soft segment is in the range of from about 8,000 to about 50,000.

30. The nonwoven web of claim 29, in which the weight average molecular weight of said soft segment is in the range of from about 8,000 to about 30,000.

31. The nonwoven web of claim 30, in which the average molecular weight of said soft segment is in the range of from about 8,000 to about 16,000.

32. The nonwoven web of claim 28, in which said soft segment is present in the range of from about 90 to about 97 percent by weight.

33. The nonwoven web of claim 32, in which said soft segment is present in the range of from abut 95 percent to about 97 percent by weight.

34. The nonwoven web of claim 28, in which said hard segment is present in the range of from about 3 to about 10 percent by weight.

35. The nonwoven web of claim 34, in which said hard segment is present in the range of from about 3 to about 5 percent by weight.

36. The nonwoven web of claim 28, in which said soft segment is derived from a poly(oxyethylene) diol.

37. The nonwoven web of claim 36, in which said hard segment is a polyurethane.

38. The nonwoven web of claim 37, in which said polyurethane is derived from 1,4-butanediol.

39. A nonwoven web comprising a matrix of meltblown thermoplastic polymeric fibers and a multiplicity of individualized fibers disposed throughout said matrix and engaging at least some of the matrix fibers to space said matrix fibers apart from each other, said individualized fibers being interconnected by and held captive within said matrix by mechanical entanglement of said matrix fibers with said individualized fibers, the mechanical entanglement and interconnection of said matrix fibers and individualized fibers alone forming a coherent integrated fibrous structure, in which either said matrix fibers or said individualized fibers are composed of a superabsorbent, thermoplastic polymer composition comprising:

(A) from about 86 to about 98 percent by weight, based on the total weight of the composition, of a poly(oxyethylene) soft segment having a weight average molecular weight in the range of from about 5,000 to about 50,000; and (B) from about 2 to about 14 percent by weight, based on the total weight of the composition, of a hard segment which has a melting point above ambient temperature and below the temperature at which decomposition of either the composition or the soft segment takes place, is essentially insoluble in water, and phase separates from the soft segment, said hard segment being selected from the group consisting of polyurethanes, polyamides, polyesters, polyureas, and combinations thereof;

wherein the soft and hard segments are covalently bound together by means of urethane, amide, ester, or secondary urea linkages or combinations thereof.

40. The nonwoven web of claim 39, in which the weight average molecular weight of said soft segment is in the range of from about 8,000 to about 50,000.

41. The nonwoven web of claim 40, in which the weight average molecular weight of said soft segment is in the range of from about 8,000 to about 30,000.

42. The nonwoven web of claim 41, in which the weight average molecular weight of said soft segment is in the range of from about 8,000 to about 16,000.

43. The nonwoven web of claim 39, in which said soft segment is present in the range of from about 90 to about 97 percent by weight.

44. The nonwoven web of claim 43, in which said soft segment is present in the range of from about 95 percent to about 97 percent by weight.

45. The nonwoven web of claim 39, in which said hard segment is present in the range of from about 3 to about 10 percent by weight.

46. The nonwoven web of claim 45, in which said hard segment is present in the range of from about 3 to about 5 percent by weight.

47. The nonwoven web of claim 39, in which said soft segment is derived from a poly(oxyethylene) diol.

48. The nonwoven web of claim 47, in which said hard segment is a polyurethane.

49. The nonwoven web of claim 48, in which said polyurethane is derived from 1,4-butanediol.

* * * * *